United States Patent [19]

Just et al.

[11] 3,988,372

[45] Oct. 26, 1976

[54] ENAMINE INTERMEDIATES FOR PRODUCING PROSTAGLANDINS

[75] Inventors: George E. Just, Westmount, Canada; Chaim Simonovitch, Rishon-Le-Zion, Israel

[73] Assignee: George E. Just, Westmount, Canada

[22] Filed: July 21, 1975

[21] Appl. No.: 597,457

Related U.S. Application Data

[60] Division of Ser. No. 281,341, Aug. 17, 1972, Pat. No. 3,920,643, which is a continuation of Ser. No. 103,334, Dec. 31, 1970, abandoned, which is a continuation-in-part of Ser. No. 657,085, July 31, 1967, abandoned.

[30] Foreign Application Priority Data

Aug. 9, 1966 United Kingdom............... 35550/66

July 5, 1967 United Kingdom................ 3588/67

[52] U.S. Cl............................................ 260/563 R
[51] Int. Cl.$^2$................ C07C 87/02; C07C 175/00
[58] Field of Search......... 260/563 R, 468 D, 563 A

[56] References Cited

UNITED STATES PATENTS

| | | | |
|---|---|---|---|
| 2,216,548 | 10/1940 | Converse | 260/563 R X |
| 3,153,650 | 10/1964 | Johnson | 260/563 R X |

*Primary Examiner*—Allen B. Curtis

[57] ABSTRACT

Prostaglandin $F_{1\alpha}$, prostaglandin $F_{1\beta}$, and analogs of those are produced from bicyclo[3.1.0]hexane intermediates.

4 Claims, No Drawings

ENAMINE INTERMEDIATES FOR PRODUCING PROSTAGLANDINS

CROSS REFERENCE TO RELATED APPLICATION

This application is a division of copending application Ser. No. 281,341, filed Aug. 17, 1972 now U.S. Pat. No. 3,920,643, which is a continuation of copending application Ser. No. 103,334, filed Dec. 31, 1970, and now abandoned, which is a continuation-in-part of copending application Ser. No. 657,085, filed July 31, 1967, and now abandoned.

DESCRIPTION OF THE INVENTION

This invention relates to compositions of matter, and to methods and intermediates for producing them. In particular, this invention relates to novel analogs of prostaglandin $F_1$ and the novel analogs thereof, and to novel chemical intermediates useful in those methods.

$PGF_{1\alpha}$ has the following structure:

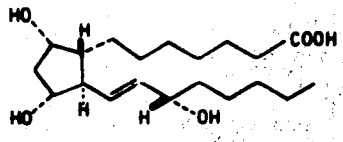

$PGF_{1\beta}$ has the following structure:

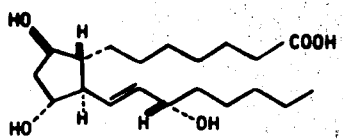

See footnote (3) in J. Am. Chem. Soc. 88, 3133 (1966), and Nature, 212, 38 (1966) for discussion of the stereochemistry of $PGF_{1\alpha}$ and $PGF_{1\beta}$.

In formulas I and II, as well as in the formulas given hereinafter, broken line attachments to the cyclopentane ring indicate hydrogen or other substituents in alpha configuration, i.e., below the plane of the cyclopentane ring. Heavy solid line attachments to the cyclopentane ring indicate hydrogen or other substituents in beta configuration, i.e., above the plane of the cyclopentane ring.

$PGF_{1\alpha}$ and $PGF_{1\beta}$ are derivatives of prostanoic acid which has the following formula and atom numbering:

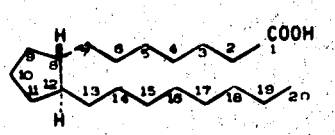

A systematic name for prostanoic acid is 7-[(2β-octyl)-cyclopent-1α-yl]heptanoic acid.

Compounds similar to formula III but with carboxyl-terminated side chain attached to the cyclopentane in beta configuration are designated 8-iso-prostanoic acids, and have the following general formula:

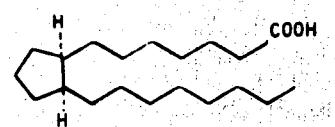

A systematic name for iso-prostanoic acid is 7-[(2β-octyl)cyclopent-1β-yl]heptanoic acid.

The prostaglandin F analogs produced according to the novel methods of this invention are represented by the formula:

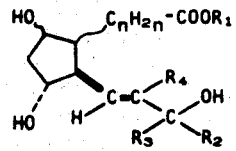

wherein ~ is a generic expression denoting an alpha or a beta configuration for the attached moiety, the side-chain-OH is in S or R (epi) configuration, $R_1$ is hydrogen, alkyl of 1 to 8 carbon atoms, inclusive, cycloalkyl of 3 to 10 carbon atoms, inclusive, aralkyl of 7 to 10 carbon atoms, inclusive, phenyl, or phenyl substituted by 1 to 3 chloro or alkyl of 1 to 4 carbon atoms, inclusive, $R_2$ is hydrogen or alkyl of 1 to 8 carbon atoms, inclusive, $R_3$ and $R_4$ are hydrogen or alkyl of 1 to 4 carbon atoms, inclusive, and $C_nH_{2n}$ is alkylene of 1 to 8 carbon atoms, inclusive, and pharmacologically acceptable salts thereof when $R_1$ is hydrogen, excluding the compound known as $PGF_{1\alpha}$ and $PGF_{1\beta}$ and their salts.

Formula V represents $PGF_{1\alpha}$ and when $C_nH_{2n}$ is hexamethylene, $R_2$ is pentyl, $R_1$, $R_3$, and $R_4$ are each hydrogen, the attachments of both —OH and —$C_nH_{2n}$—$COOR_1$ to the cyclopentane ring are in alpha configuration (dotted line), and the configuration of the side-chain —OH is S.

Formula V represents $PGF_{1\beta}$ and when $C_nH_{2n}$ is hexamethylene, $R_2$ is pentyl, $R_1$, $R_3$, and $R_4$ are each hydrogen, the —OH adjacent —$C_nH_{2n}$—$COOR_1$ is attached to the cyclopentane ring in beta configuration, the other —OH and the —$C_nH_{2n}$—$COOR_1$ are both attached to the cyclopentane ring in alpha configuration, and the configuration of the side-chain —OH is S.

All compunds encompassed by formula V have the —CH=$CR_4CR_2R_3$OH side chain attached in beta configuration with a trans C=C linkage, both as shown in that formula.

With regard to formula V examples of alkyl of 1 to 4 carbon atoms, inclusive, are methyl, ethyl, propyl, butyl, and isomeric forms thereof. Examples of alkyl of 1 to 8 carbon atoms, inclusive, are those given above, and pentyl, hexyl, heptyl, octyl, and isomeric forms thereof. Examples of cycloalkyl of 3 to 10 carbon atoms, inclusive, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 3-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl. Examples of aralkyl of 7 to 10 carbon atoms, inclusive, are benzyl, phenethyl, 1-phenylethyl, 2-phenylpropyl, 4-phenylbutyl, and 3-phenylbutyl. Examples of phenyl substituted by 1 to 3 chloro or alkyl of 1 to 4 carbon atoms, inclusive, are p-chlorophenyl, m-chlorophenyl, o-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4- chloro-2-methylphenyl, and 2,4-dichloro-3-methylphenyl.

Examples of alkylene of 1 to 8 carbon atoms, inclusive, are methylene, ethylene, trimethylene, tetramethylene, pentamethylene, hexamethylene, heptamethylene, octamethylene, and isomeric branched chain forms thereof.

$PGF_{1\alpha}$ and $PGF_{1\beta}$ are known compounds, and they and their esters, acylates, and pharmacologically acceptable salts are extremely potent in causing various biological responses. For that reason, these compounds are useful for pharmacological purposes. See Horton, Experientia, 21, 113 (1965); Samuelsson, Angew. Chem. intern. Ed. Eng. 4, 410 (1965); Bergstrom et al., Ann. Rev. Biochem. 34, 101 (1965), Bergstrom, Recent Prog. Horm. Res. 22, 153 (1966), Bergstrom et al., Pharmacol. Rev. 20, 1 (1968), and references cited in those. A few of these biological responses are systemic arterial blood pressure lowering in the case of the $PGF_{1\beta}$ compounds as measured, for example, in anesthetized (pentobarbital sodium) pentolinium-treated rats with indwelling aortic and right heart cannulas; pressor activity, similarly measured, for the $PGF_{1\alpha}$ compounds; stimulation of smooth muscle as shown, for example, by tests on strips of guinea pig ileum, rabbit duodenum, or gerbil colon; potentiation of other smooth muscle stimulants; antipolytic activity as shown by antagonism of epinephrine-induced mobilization of free fatty acids or inhibition of the spontaneous release of glycerol from isolated rat fat pads; and decrease of blood platelet adhesiveness as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen.

Because of their biological responses, these known prostaglandins are useful to study, prevent, control, or alleviate a wide variety of diseases and undesirable physiological conditions in birds and mammals, including humans, useful domestic animals, pets, and zoological speciments, and in laboratory animals, for example, mice, rats, rabbits and monkeys.

For example, these compounds are useful in mammals, including man, as nasal decongestants. For this purpose, the compounds are used in a dose range of about 10 μg. to about 10 mg. per ml. of a pharmacologically suitable liquid vehicle or as an aerosol spray, both for topical application.

The $PGF_{1\alpha}$ and $PGF_{1\beta}$ compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.005 to about 20 mg. per kg. of body weight per day are used, the exact dose depending on the age, weight, and condition of the patient or animal, and on the frequency and route of administration.

The $PGF_{1\alpha}$ and $PGF_{1\beta}$ compounds are especially useful as additives to blood, blood products, blood substitutes, and other fluids which are used in artifical extracorporeal circulation and perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of those at a total steady state dose of about 0.001 to 10 mg. per liter of circulating fluid. It is especially useful to use these compounds in laboratory animals, e.g., cats, dogs, rabbits, monkeys, and rats, for these purposes in order to develop new methods and techniques for organ and limb transplants.

The $PGF_{1\beta}$ compounds are useful as hypotensive agents to reduce blood pressure in mammals including man. For this purpose, the compounds are administered by intravenous infusion at the rate about 0.01 to about 50 μg. per kg. of body weight per minute, or in single or multiple doses of about 25 to 500 μg. per kg. of body weight total per day.

The $PGF_{1\alpha}$ and $PGF_{1\beta}$ compounds are useful in place of oxytocin to induce labor in pregnant female animals, including man, cows, sheep, and pigs, at or near term, or in pregnant animals with intrauterine death of the fetus from about 20 weeks to term. For this purpose, the compound is infused intravenously at a dose 0.01 to 50 μg. per kg. of body weight per minute until or near the termination of the second stage of labor, i.e., expulsion of the fetus. These compounds are especially useful when the female is one or more weeks postmature and natural labor has not started, or 12 to 60 hours after the membranes have ruptured and natural labor has not yet started.

The $PGF_{1\alpha}$ and $PGF_{1\beta}$ compounds are useful for controlling the reproductive cycle in ovulating female mammals, including humans and other animals. For that purpose $PGF_{1\alpha}$, for example, is administered systemically at a dose level in the range 0.1 mg. to about 50 mg. per kg. of body weight, advantageously during a span of time starting approximately at the time of ovulation and ending approximately at the time of menses or just prior to menses. Additionally, expulsion of an embryo or a fetus is accomplished by similar administration of the compound during the first third of the normal mammalian gestation period.

The compounds other than $PGF_{1\alpha}$ and $PGF_{1\beta}$ and their esters encompassed by formula V each cause the biological responses described above for the $PGF_{1\alpha}$ and $PGF_{1\beta}$ compounds, and each of those other compounds is accordingly useful for the abovedescribed correponding purposes, and is used for those purposes in the same manner as described above.

$PGF_{1\alpha}$ and $PGF_{1\beta}$ are known to be potent in causing multiple biological responses even at low doses. In striking contrast, the $PGF_{1\alpha}$ and $PGF_{1\beta}$ analogs also encompassed by formula V are substantially more specific with regard to potency in causing prostaglandin-like biological responses. Therefore, these prostaglandin F analogs are surprisingly and unexpectedly more useful than the known prostaglandins F for at least one of the pharmacological purposes indicated above for the latter. Use of the analog for that purpose results in smaller undesired side effects than when the known prostaglandin F is used. For these same purposes, the formula V 8-iso analogs are especially preferred.

To obtain the optimum combination of biological response specificity and potency, certain of the compounds within the scope of formula V are preferred. For example, it is preferred that $C_nH_{2n}$ in formula V be limited to alkylene of 5 to 8 carbon atoms, inclusive, with at last 5 carbon atoms between the ring and $COOR_1$. Examples of these alkylene are pentamethylene unsubstituted or substituted with one, 2, or 3 alkyl carbon atoms, hexamethylene unsubstituted or substituted with one or 2 alkyl carbon atoms, heptamethylene unsubstituted or substituted with a methyl group, and unsubstituted octamethylene. Another preference is that $R_2$ be limited to alkyl of 4 to 8 carbon atoms, inclusive. Examples of these alkyl are butyl, pentyl, hexyl, heptyl, octyl, and isomeric forms of those. Still another preference is that $R_3$ and $R_4$ be limited to hydrogen or methyl. These preferences in formula V also, of course, encompass the known compounds $PGF_1 \alpha$ and $PGF_{1\beta}$ and their esters.

The compounds of formula V, including $PGF_{1\alpha}$, $PGF_{1\beta}$, and the preferred analogs defined above, are used for the purposes described above in the free acid form, in ester form, or in pharmacologically acceptable salt form. When the ester form is used, the ester is any of those within the above definition of $R_1$. However, it is preferred that the ester be alkyl of one to 4 carbon atoms, inclusive. Of these alkyl, methyl and ethyl are especially preferred for optimum absorption of the compound by the body or experimental animal system.

Pharmacologically acceptable salts of these formula V compounds useful for the purposes described above are those with pharmacologically acceptable metal cations, ammonium, amine cations, or quaternary ammonium cations.

Especially preferred metal cations are those derived from the alkali metals, e.g.., lithium, sodium and potassium, and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methypiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2- methyl-1-propanol, tris(hydroxymethyl)aminomethane, N-phenylethanolamine, N-(p-tert-amylphenyl)-diethanolamine, galactamine, N-methylglucamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

As discussed above, the compounds of formula V are administered in various ways for various purposes; e.g., intravenously, intramuscularly, subcutaneously, orally, intravaginally, rectally, buccally, sublingually, topically, and in the form of sterile implants for prolonged action.

For intravenous injection or infusion, sterile aqueous isotonic solutions are preferred. For that purpose, it is preferred because of increased water solubility that $R_1$ in the formula V compound be hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixers, and simple solutions, with the usual pharmaceutical carriers are used for oral or sublingual administration. For rectal or vaginal administration, suppositories prepared as known in the art are used. For tissue implants, a sterile tablet or silicone rubber capsule or other object containing or impregnated with the substance is used.

As disclosed in the above-cited references, until recently, $PGF_{1\alpha}$ has been available only on milligram quantities by extruction from certain animal tissues, especially from sheep vesicular glands. $PGF_{1\alpha}$ and $PGF_{1\beta}$ have also been available in even smaller amounts by reduction of $PGE_1$ which itself is available only in milligram quantities from the same animal tissues. More recently, biosynthetic procedures have been developed for the production of these natural prostaglandins and also certain analogous compounds. See above references and U.S. Pat. No. 3,296,091, for example. Those biosynthetic procedures involve incubation of certain expensive unsaturated long chain fatty acids with certain animal tissues, especially vesicular tissues of uncastrated rams. The cost of producing prostaglandins and prostaglandin analogs by any of those prior art methods in sufficient quantity to satisfy current needs is so great as to be a limiting factor in research and pharmacological use of these substances. It is one purpose of this invention to provide methods for the production of these substances in substantial amounts and in high purity at a reasonable cost. It is another purpose of this invention to provide methods for production of useful and hitherto unavailable analogs of $PGF_{1\alpha}$ and $PGF_{1\beta}$.

$PGF_{1\alpha}$, $PGF_{1\beta}$, and the novel analogues thereof encompassed by formula V are prepared by the novel reaction sequences set forth hereinafter in Charts A and B.

In Charts A and B, the definitions of the various generic symbols $R_1$ to $R_9$ and $C_nH_{2n}$ are constant. $R_1$, $R_2$, $R_3$, $R_4$, and $C_nH_{2n}$ are as given above for formula V.

$R_5$ and $R_6$ are shown in formula XVI, Chart B, linked to nitrogen, and are defined as alkyl of 1 to 8 carbon atoms, inclusive, or alkylene linked through carbon or oxygen to form with the attached nitrogen a 5 to 7-membered heterocyclic ring.

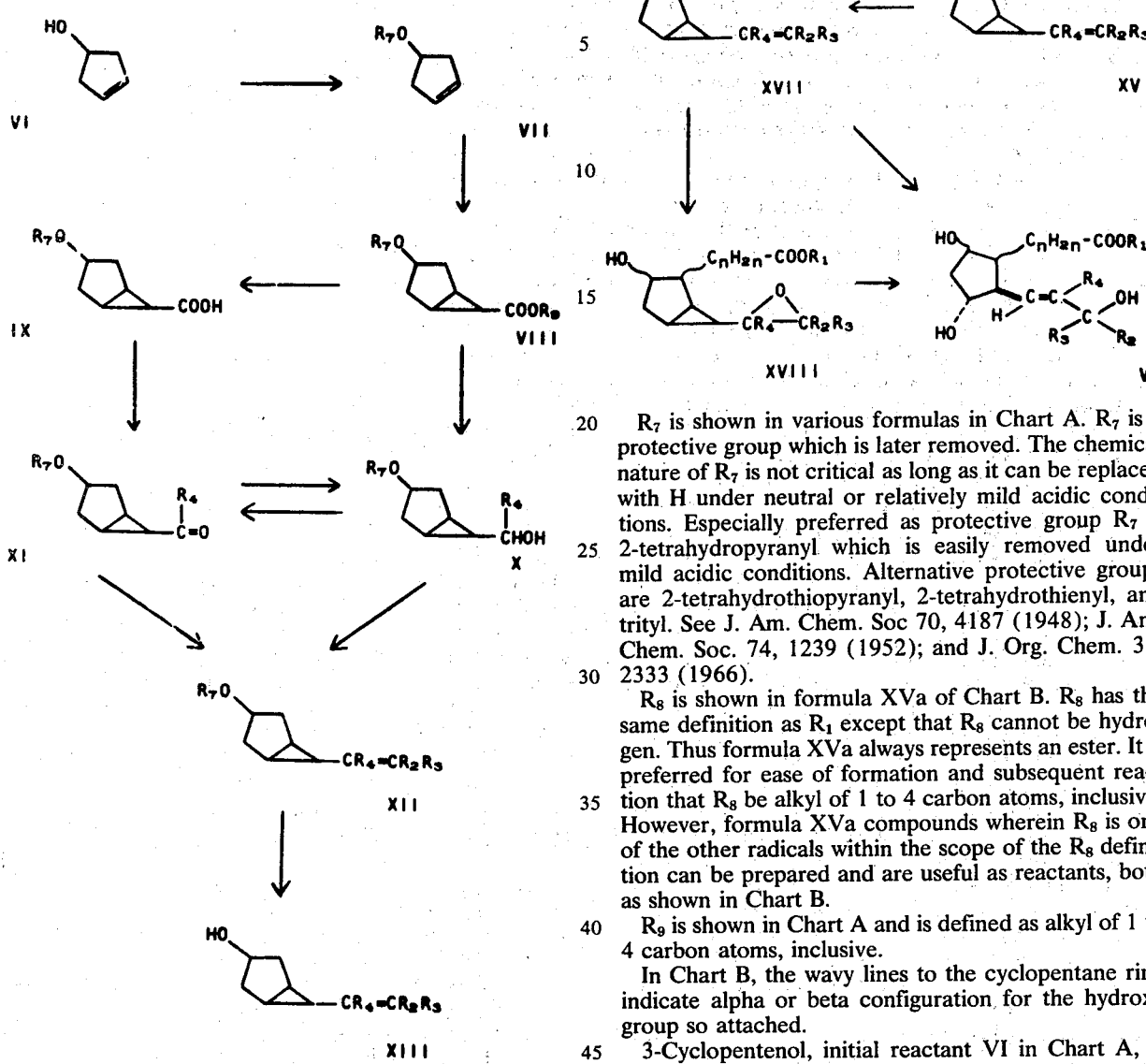

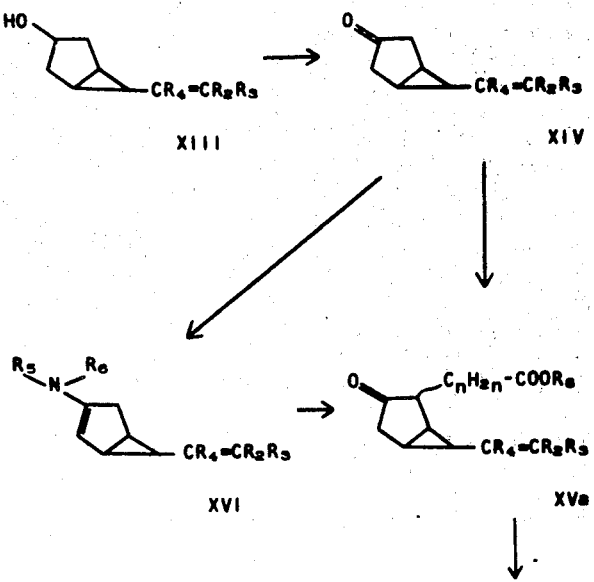

$R_7$ is shown in various formulas in Chart A. $R_7$ is a protective group which is later removed. The chemical nature of $R_7$ is not critical as long as it can be replaced with H under neutral or relatively mild acidic conditions. Especially preferred as protective group $R_7$ is 2-tetrahydropyranyl which is easily removed under mild acidic conditions. Alternative protective groups are 2-tetrahydrothiopyranyl, 2-tetrahydrothienyl, and trityl. See J. Am. Chem. Soc 70, 4187 (1948); J. Am. Chem. Soc. 74, 1239 (1952); and J. Org. Chem. 31, 2333 (1966).

$R_8$ is shown in formula XVa of Chart B. $R_8$ has the same definition as $R_1$ except that $R_8$ cannot be hydrogen. Thus formula XVa always represents an ester. It is preferred for ease of formation and subsequent reaction that $R_8$ be alkyl of 1 to 4 carbon atoms, inclusive. However, formula XVa compounds wherein $R_8$ is one of the other radicals within the scope of the $R_8$ definition can be prepared and are useful as reactants, both as shown in Chart B.

$R_9$ is shown in Chart A and is defined as alkyl of 1 to 4 carbon atoms, inclusive.

In Chart B, the wavy lines to the cyclopentane ring indicate alpha or beta configuration for the hydroxy group so attached.

3-Cyclopentenol, initial reactant VI in Chart A, is known in the art, e.g., J. Org. Chem. 25, 26 (1960).

The hydroxy group of initial reactant VI is first protected against reaction until desired by replacing the H thereof with a group $R_7$ (VII) which can later be replaced by H under neutral or mildly acidic conditions. As mentioned above, $R_7$ is preferably 2-tetrahydropyranyl, and the hydroxy H can be replaced by it by reacting VI with dihydropyran in the presence of an acidic catalyst, e.g., phosphorus oxychloride.

Protected reactant VII is next transformed to reactant VIII by reaction with an alkyl diazoacetate. The size of the alkyl group $R_9$ in the diazoacetate and in reactant VIII is not critical. Since that alkyl group is removed in subsequent transformations and does not appear in the final product, there is no reason that it be other than alkyl of 1 to 4 carbon atoms, inclusive, preferably methyl or ethyl.

Alkyl diazoacetates are known in the art, e.g., Org. Syn. 24, 56 (1944). Procedures for the addition of alkyldiazoacetates to cycloalkenes are also known in the art and such reactions usually give a mixture of exo and endo isomers, with the former usually predominating, especially in the presence of copper powder, e.g., J. Am. Chem. Soc. 85, 582 (1963); Tetrahedron Letters, No. 21, 1553 (1965).

As will be apparent from Charts A and B, the cyclopropane ring created in the transformation of VII to VIII and the stereochemistry of the attachment of the monovalent moiety to the cyclopropane ring (—COOR$_9$ in VIII) remain intact and unaltered down to the final transformation to final product V. For that final opening of the cyclopropane ring, it is preferred that the configuration of said monovalent moiety be exo, although the endo isomer is also transformed to the final desired product V as shown in Chart B. Thus there are three alternatives, carry the mixture of endo and exo isomers through to final product V, separate the endo and exo isomers of VIII or of some subsequent intermediate stage, advantageously by gas or thin layer chromatography, or isomerize the less preferred endo isomer of VIII to the preferred exo isomer of VIII, or do that isomerization at some subsequent intermediate stage. Of those alternatives, the last is preferred, the isomerization being carried out with intermediate VIII.

The isomerization of VIII is effected in high yield by treatment of VIII with an alkali metal, e.g., sodium, in the presence of an alkanol, e.g., methanol or ethanol as described in J. Am. Chem. Soc. 85, 582 (1963). If said alkanol does not correspond to R$_9$, simultaneous alcoholysis is likely to produce the formula VIII ester corresponding to said alkanol.

The configuration of the attachment of R$_7$O to the cyclopentane ring in VIII also can vary, resulting in syn and anti isomers for each of the exo and endo isomers. It is not necessary to separate those syn and anti isomers since in a subsequent step (XIII to XIV in Chart B), both isomers merge by oxidation to a single compound. Separation is accomplished if desired, however, by silica gel chromatography.

As shown in Chart A, reactant VIII is transformed to intermediate XII by several chemical routes. As will be discussed in greater detail below, the transformation of carbonyl compound XI (ketone or aldehyde depending on R$_4$) to XII is by a Wittig reaction which adds =CR$_2$R$_3$. The transformation of alcohol X (primary or secondary depending on R$_4$) to XII is by a reverse Wittig reaction which also adds =CR$_2$R$_3$.

Consider first, Chart A process VIII to X wherein R$_4$ is H. This is a reduction of a carboxylate ester group —COOR$_9$ to an alcohol group, and is effected with a variety of reducing agents, e.g., lithium aluminum hydride, a dialkyl aluminum hydride, diborane, or a mixture of an alkali metal, e.g., sodium, and an alkanol, e.g., ethanol. Procedures for carrying out this type of reduction with those reducing agents will be obvious to those skilled in this art.

Consider next Chart A process VIII to IX. This is a simple ester saponification, and is carried out by any of the known saponification methods which will not remove R$_7$.

Consider next Chart A process IX to XI wherein R$_4$ is hydrogen. This is carried out by transformation of the —COOH of IX to —COCl, for example, by reaction of IX with thionyl chloride. The intermediate acid chloride is then reduced to aldehyde XI (R$_4$ is H), for example, by the Rosenmund reduction. See "Organic Reactions", John Wiley and Sons, inc., New York, N. Y., Vol. 8, pp. 218–257 (1954) for this and other suitable methods for transforming carboxylic acids to aldehydes.

Consider next Chart A process IX to XI wherein R$_4$ is alkyl of 1 to 4 carbon atoms, inclusive. This is carried out by reacting the intermediate acid chloride of IX, mentioned above, with an organometallic compound, preferably a dialkylcadmium or an alkylcadmium halide. See "Organic Reactions", ibid., pp. 28–58.

Chart A shows X and XI as interconvertible. However, when X wherein R$_4$ is alkyl of 1 to 4 carbon atoms, inclusive, is desired, it is preferred to prepare that by reduction of XI rather than directly from VIII. When X wherein R$_4$ is H is desired, it is preferred to prepare that directly by reduction of VIII as described above. When XI wherein R$_4$ is H is desired, it is preferred to prepare that by oxidation of X wherein R$_4$ is H. When XI wherein R$_4$ is alkyl of 1 to 4 carbon atoms, inclusive, is desired, it is preferred to prepare that from IX through the acid chloride, as described above.

The reduction of XI to X wherein R$_4$ is either H or alkyl of 1 to 4 carbon atoms, inclusive, is carried out by any of the methods known for reduction of >C=O to >CHOH, for example, with lithium aluminum hydride, sodium borohydride, or catalytic hydrogenation. Procedures for carrying out that reduction are known to the art.

The oxidation of X to XI wherein R$_4$ is H is carried out by any oxidizing agent which is not sufficiently acidic to remove R$_7$. An especially useful reagent for this purpose is the Jones reagent, i.e., acidic chromic acid. See, for example, Bowden et al., J. Chem. Soc. 39 (1946). Acetone is a suitable solvent for this purpose, and a slight excess of oxidant and temperatures at least as low as about 0° C., preferably about —10° to about —20° C. should be used. The oxidation proceeds rapidly and is usually complete in about 5 to about 30 minutes. Excess oxidant is destroyed, for example, by addition of a lower alkanol, advantageously isopropyl alcohol, and the aldehyde is isolated by conventional methods, for example, by extraction with a suitable solvent, e.g., diethyl ether. Other oxidizing agents can also be used. Examples are mixtures of chromium trioxide and pyridine or mixtures of dicyclohexylcarbodiimide and dimethyl sulfoxide. See, for example, J. Am. chem. Soc. 87, 5661 (1965).

These various transformations of VIII to X and XI will, of course, give syn and anti isomers, and exo and endo isomers, depending upon the stereochemical nature of VIII. As mentioned above, there is no need to separate these isomers at any stage, but that can be done.

The transformation of reactant XI to intermediate XII involves the Wittig reaction. Procedures for the Wittig reaction are well known in the art. See, for example, Tetrahedron Letters 2503 (1964), Chem. and Ind. 507 (1955), and Quart. Rev. XVII, No. 4, 406 (1963). The Wittig reagent to be used in this transformation has the formula

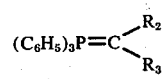   XIX wherein C$_6$H$_5$ represents phenyl, and R$_2$ and R$_3$ are as defined above. Reagent XIX is prepared by reacting triphenylphosphine with an alkyl chloride or bromide of the formula

wherein X is Cl or Br, to produce an alkyltriphenylphosphonium halide. Hydrogen halide is eliminated from that phosphonium bromide by reaction with a base, for example, sodium or potassium hydride, sodium or potassium amide, an alkyl or phenyl lithium, or sodium or potassium hydroxide. At least one mole, and preferably 2 to 8 moles, of this formula XIX reagent is reacted with each mole of the formula XI reactant. The reaction is usually carried out in the presence of an inert diluent, e.g., diethyl ether, benzene, toluene, hexane, dimethylsulfoxide, tetrahydrofuran, dichloromethane, or chlorform, at temperatures between 0° C. and the reflux temperature of the reaction mixture. The reaction is often complete within a few hours, although the reaction usually takes longer when $R_4$ in formula XI is alkyl of 1 to 4 carbon atoms. The desired formula XII unsaturated product is isolated from the reaction mixture by conventional methods, for example, evaporation of the solvent or addition of water and extraction with a water-immiscible diluent, e.g., diethyl ether.

The transformation of alcohol reactant X to product XII is also carried out by a Wittig reaction the reverse of the formula XI to XII transformation. In the case of X to XII, however, the X compound is transformed directly to the triphenylphosphorane by reaction first with triphenylphosphine hydrobromide or hydrochloride, and then with a base. Alternatively, the OH of the formula X compound is transformed to bromide or chloride by the usual procedures, and that halide reacted first with triphenylphosphine and then with a base. Then the phosphorane is reacted with an aldehyde or ketone

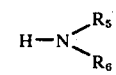

wherein $R_2$ and $R_3$ are as defined above. Known procedures similar to the transformation of XI to XII, described above, are used for this reverse Wittig.

A mixture of cis and trans isomers of the formula XII product is obtained by these Wittig reactions. Also during the reaction, the $R_7$ group is sometimes replaced with hydrogen. Therefore it is preferred that the $R_7$ group be removed completely before any attempt is made to separate these cis and trans isomers.

The transformation of the formula XII intermediate to the formula XIII hydroxy product is carried out by any method with replaces $R_7$ with H without altering the rest of the molecule. When, as preferred, $R_7$ is 2-tetrahydropyranyl, this transformation is carried out by mixing reactant XII with a strong acid, for example, oxalic acid. See J. Am. Chem. Soc. 70, 4187 (1948) and J. Am. Chem. Soc. 74, 1239 (1952) for suitable procedures. Silver ion is used to transform $R_7$ is H when $R_7$ is 2-tetrahydrothiopyranyl or 2-tetrahydrothienyl. See J. Org. Chem. 31, 2333 (1966).

Cis and trans isomers of XIII are separated, advantageously with silica gel chromatography. However, since syn and anti isomers also can be present for both the cis and trans isomers, there is advantage in oxidizing the OH of formula XIII to a carbonyl (XIV) before cis and trans isomer separation is carried out.

The transformation of reactant XIII to intermediate product XIV is carried out by oxidation with any reagent which does not alter the rest of the molecule, especially the $-CR_4=CR_2R_3$ moiety. Such reagents are known to the art. An especially useful reagent for this purpose is the Jones reagent mentioned above for the transformation of alcohol X to carbonyl compound XI.

The cis and trans isomers of compound XIV are separable by silica gel chromatography, advantageously with silver nitrate present in the silica gel.

Consider next Chart B process XIV to XVa. This is an alkylation process whereby the moiety $-C_nH_{2n}-COOR_8$ is introduced into the bicyclo ring system adjacent to the carbonyl group. Two isomers are possible for this alkylation product XVa, alpha or beta. Both isomers are obtained in the alkylation processes described hereinafter. Any of the prior art alkylation procedures can be used for this alkylation One useful alkylation procedure proceeds through an intermediate enamine XVI. That enamine is prepared by mixing the formula XIV olefin ketone with a secondary amine of the formula

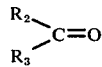

wherein $R_5$ and $R_6$ are alkyl or alkylene linked together through carbon or oxygen to form together with the nitrogen a 5 to 7-numbered heterocyclic ring. Examples of suitable amines are diethylamine, dipropylamine, dibutylamine, dihexylamine, dicotylamine, dicyclohexylamine, methylcyclohexylamine, pyrrolidine, 2-methylpyrrolidine, piperidine, 4-methylpiperidine, morpholine, hexamethylenimine, and the like.

The Formula XVI enamine is prepared by heating a mixture of the formula XIV olefin ketone with an excess of the amine preferably in the presence of a strong acid catalyst such as an organic sulfonic acid, e.g., p-toluenesulfonic acid, or an inorganic acid, e.g., sulfuric acid. it is also advantageous to carry out this reaction in the presence of a water-immiscible diluent, e.g., benzene or toluene, and to remove water by azeotropic distillation as it is formed during the reaction. Then, after water formation ceases, the enamine is isolated by conventional methods.

The Formula XVI enamine is then reacted with a haloester, $X-C_nH_{2n}-COOR_8$ to give the desired formula VIIIa product. This reaction of the enamine is carried out by the usual procedures. See "Advances in Organic Chemistry." Interscience Publishers, New York, N.Y., Vol. 4, pp. 25–47 (1963) and references cited therein. In addition to halogen, X in $X-C_nH_{2n}-COOR_1$ can also be tosylate, mesylate, and the like. It is especially preferred that X be bromine or iodine. Dimethylsulfoxide is especially useful as a diluent in the reaction of the enamine with the haloester.

The alkylation reaction XIV to XVa can also be carried out directly with the same haloester used in the enamine process. Any of the usual alkylation bases, e.g. alkali metal hydrides, alkali metal amides, and alkali metal alkoxides can be used for this alkylation. Alkali metal alkoxides are preferred, especially the tert.alkoxides. Sodium and potassium are preferred alkali metals. Expecially preferred is potassium tert.butoxide. Preferred diluents for this direct alkylation are tetrahydrofuran and 1,2-dimethoxyalkane. Otherwise, procedures for producing and isolating the desired formula XVa product are known in the art.

The two isomeric formula XVa products, alpha and beta, obtained by either alkylation procedure, i.e., direct or through the enamine, can be separated by chromatographic procedures known in the art and exemplified hereinafter.

The formula XVa product is an ester, and is hydrolyzed or saponified by methods known in the art to the formula XV product wherein $R_1$ is hydrogen. It is preferred for ease of alkylation that $R_8$ in XVa be alkyl of 1 to 4 carbon atoms, inclusive, and that when $R_1$ is to be other than hydrogen or alkyl of 1 to 4 carbon atoms, it is preferred that the formula XV compound be prepared by esterification of the formula XV compound wherein $R_1$ is hydrogen.

In Chart B, ketone XV is reduced to hydroxy compound XVII which is then used as a reactant to produce a final PGF-type compound V. That reduction of XV to XVII is advantageously carried out with sodium borohydride, although any reducing agent which transforms a ketonic carbonyl to a hydroxy group without altering the ester group —$COOR_1$ or the —$CR_4$=$CR_2R_3$ moiety can be used. Two isomeric hydroxy compounds are produced by this XV to XVII reduction, alpha and beta. Those isomers are separated by chromatographic procedures known in the art and exemplified below.

Referring now to Chart B, the final process steps to produce $PGF_1$-type compounds of formula V are shown as XVII to V and XVIII to XV. Epoxide XVIII is prepared from XVII.

The epoxidation reaction XVII to XVIII is carried out by mixing olefin XVII with a peroxy compound which is hydrogen peroxide or an organic percarboxylic acid. Any of the isomers or mixtures thereof represented by formula XVII is used as a reactant. An organic percarboxylic acid is preferred for these transformations. Examples of useful organic percarboxylic acids for this purpose are performic acid, peracetic acid, perlauric acid, percamphoric acid, perbenzoic acid, m-chloroperbenzoic acid, and the like. Perlauric acid and m-chloroperbenzoic acid are especially preferred.

The peroxidation is advantageously carried out by mixing the formula XVII olefin with about one equivalent of the per acid or hydrogen peroxide, advantageously in a diluent, for example, chloroform. The reaction usually proceeds rapidly, and the formula XVIII oxide is isolated by conventional methods, for example, evaporation of the reaction diluent and removal of the acid corresponding to the per acid if one is used. It is usually unnecessary to purify the oxide before using it in the next step. This epoxidation can be carried out either on the ester or the free acid of the olefin reactant.

Referring again to the unsaturated hydroxy side chain in V, the C=C will always be trans as shown regardless of the cis-trans isomerism of olefin XVII, or of the isomerism of epoxides XVIII. Also the unsaturated hydroxy side chain is always attached as shown to the cyclopentane ring in beta configuration. The hydroxy adjacent to the unsaturated hydroxy side chain in V will always be alpha.

The configuration of the —$C_nH_{2n}$—COOR moiety in V, i.e., alpha or beta, will depend on the configuration of the same moiety in the reactants XVII and XVIII, since that configuration is not changed during the transformations to V. Also, the configuration of the —OH attached to the cyclopentane ring in XVII and XVIII does not change during transformation of those to V.

Thus mixtures of formula V isomers are always obtained, and the stereochemical nature of those mixtures will depend on the stereochemistry of the reactant. However, each formula V product is useful for the pharmacological uses set forth hereinabove.

The transformation of epoxide XVIII to V is carried out by mixing said epoxide with a reactant acid which is (1) an organic acid with pK less than 4, (2) a mixture of an organic acid with pK 4 to 6 and a catalytic amount of an acid with pK less than 2, (3) an inorganic acid with pK less than 4, (4) a Lewis acid, or (5) mixtures of those.

The transformation of reactant XVII to V combines the conditions for XVIII to V. In other words, said peroxy compound is mixed with said reactant acid. For this direct route XVII to V, it is preferred that the peroxy compound be hydrogen peroxide, preferably 30 to 90% aqueous solutions. The peroxy compound XVIII may be intermediates in the direct route, although that is not certain.

As a reactant acid, organic acids with pK less than 4 are preferred. Examples of such acids are formic acid, chloroacetic acid, trichloroacetic acid, fluoroacetic acid, trifluoroacetic acid, oxalic acid, maleic acid, and the like. Especially preferred are formic acid and trifluoroacetic acid.

Examples of organic acids with pK 4 to 6 include most of the known organic carboxylic acids as well as some of the known negatively-substituted phenols. Examples are the alkanoic acids, e.g., acetic acid. The most useful acids with pK less than 2 are the so-called mineral acids, i.e., hydrochloric acid, hydrofluoric acid, sulfuric acid, and perchloric acid. Examples of the most useful inorganic acids with pK less than 4 are the same as the mineral acids mentioned above. Examples of Lewis acids are magnesium bromide, zinc acetate, zinc formate, zinc bromide and boron trifluoride. Oxygen is, of course, necessary at one stage in production of the final formula V product, and some of the initial reaction products, especially with acids containing no oxygen, must be mixed or "quenched" with water, or small amounts of water must be present in the reaction mixture, e.g., moist non-aqueous diluents.

When an organic acid or inorganic oxy acid is used for this final transformation, the initial product is often an ester rather than the desired formula V hydroxy compound. Those esters are usually easily transformed to the hydroxy compound by alkaline hydrolysis under mild conditions, preferably below about 25° C., more preferably below about 10° C.

Especially when $R_1$ in the formula XVII and XVIII reactant is hydrogen, when an organic acid with pK less than 4 is used, it is preferred to add to the reaction mixture an alkali metal or alkaline earth metal salt of such an acid, advantageously of the same acid. At least one equivalent of the salt per equivalent of organic reactant should be used, advantageously 2 to 20 equivalents or even more. Particularly preferred for any of these final transformations is a mixture of formic acid and an alkali metal formate, e.g., sodium formate.

Examples of the preferred reaction conditions are set forth hereinafter.

As mentioned above, mixtures of stereoisomeric formula V products are obtained. These are separated into the individual isomers by methods known in the art, advantageously by preparative thin layer chromatography.

Racemic formula V $PGF_1$ products are, of course, obtained from racemic intermediates. If optically active formula V products are desired, the free acid forms of those are subjected to resolution by methods known in the art. In this regard, however, it is advantageous to resolve an intermediate, preferably the formula XV or formula XVII reactant since those are chemically and thermally more stable than the final products.

The invention can be more fully understood by the following examples:

Infrared spectra are determined on undiluted liquid samples, and are indicated as γ in cm$^{-1}$. Nuclear magnetic resonance spectra are based on tetramethylsilane as an internal standard. Deuterochloroform is used as solvent, and the spectra are reported as (chemical shifts) in parts per million (p.p.m.).

EXAMPLE 1

Tetrahydropyranyl ether of 3-cyclopentenol (VII)

A mixture of 3.29 g. of 3-cyclopentenol (VI) and 3.39 g. of dihydropyran is cooled to 0° C., and two drops of phosphorus oxychloride are added. The mixture is stirred for 1 hr. at 0° C. and 4 hrs. at room temperature (about 25° C.). The mixture is then diluted with diethyl ether, and washed first with 10% aqueous potassium hydroxide and then with water. The diethyl ether solution is dried over magnesium sulfate and evaporated. Chromatography from hexane on aluminum oxide of activity I gives the tetrahydropyranyl ether of 3-cyclopentenol (VII) in 90% yield as a liquid, b.p. 110° at 20 mm.; $N_D^{21.5}$ 1.4709; γ 3070, 1625, 1140, and 1070 cm$^{-1}$.; δ 5.42, 2.24, 1.37, 3.52, 4.45 (broad) p.p.m.

Analysis: Calcd. for $C_{10}H_{16}O_2$: C, 71.32; H, 9.59. Found: C, 71.59; H, 9.27.

EXAMPLE 2

Ethyl 3-[tetrahydropyran-2-yl)oxy]bicyclo[3.1.0]hexane-6-carboxylate (VIII)

A mixture of 0.01 M of the tetrahydropyranyl ether of 3-cyclopentenol (VII) and 1 g. of copper powder is stirred vigorously and maintained at 100° C. while 0.07 M (8 g.) of ethyl diazoacetate is added over a period of 8 hours. The reaction mixture is then extracted with hexane and chromatographed over aluminum oxide (activity I). Elution first with hexane, and then benzene, and evaporation of the eluates gives ethyl 3-[(tetrahydropyran-2-yl)oxy]bicyclo[3.1.0]hexane-6-carboxylate (VIII) in 55% yield as a liquid, b.p. 133° at 1.1 mm.; λ max. 195 mmμ (pentane); γ 3100, 3075, 3047, 1725, 1272, 1140 and 1020 cm$^{-1}$.; δ 3.92 (quartet), 1.07 (triplet) p.p.m.

Analysis: Calcd. for $C_{14}H_{22}O_4$: C, 66.11; H, 8.72. Found: C, 66.60; H, 8.59.

Gas-liquid chromatographic analysis of the ethyl 3-[(tetrahydropyran-2-yl)oxy]bicyclo[3.1.0]hexane-6-carboxylate (VIII) obtained as above shows that the product is a mixture of exo and endo isomers in a 4:1 ratio. A solution of 2.8 g. of the above mixture of isomers and 150 mg. of sodium methoxide in 50 ml. of methanol is heated under reflux for 4 hrs. The mixture then is evaporated, the residue extracted with diethyl ether, and the diethyl ether extract evaporated to give the exo isomer of methyl 3-[(tetrahydropyran-2-yl)oxy]bicyclo[3.1.0]hexane-6-carboxylate as an oil; b.p. 130°–133° at 1.1 mm.; homogenous as to the exo isomer by gas-liquid chromatographic analysis and by thin layer chromatographic analysis (silica, developed with benzene-ether 5:1).

Treating the tetrahydropyranyl ether of 3-cyclopentenol with other diazoacetic esters, for example, propyl or butyl diazoacetate, produces the corresponding ester of compound (VIII) for example, propyl or butyl 3-[(tetrahydropyran-2-yl)oxy]bicyclo[3.1.0]hexane-6-carboxylate.

EXAMPLE 3

Methyl 3-[(tetrahydropyran-2-yl)oxy]bicyclo[3.1.0]hexane-6-carboxylate (VIII)

A mixture of 26.5 g. of the tetrahydropyranyl ether of 3-cyclopentenol and 3 g. of copper powder is heated to 95°–100° C. bath temperature while stirring vigorously. Ethyl diazoacetate (97 g.) is then added slowly during 4 hours at a bath temperature 90°–105° C. so that the reaction mixture stays covered with foam due to evolving nitrogen. The resulting reaction mixture is cooled to 25° C., and 140 ml. of diethyl ether is added. Filtration through Celite and evaporation of the diethyl ether gives 84.7 g. of a red oil. This oil is chromatographed on 2000 g. of silica gel. After elution of unreacted starting material (VII) with dichloromethane, elution with a mixture of isomeric hexanes and ethyl acetate (90:10), and evaporation of the eluate, gives 23 g. of a colorless oil which shows two peaks, the syn and anti isomers of the exo form of ethyl 3-[(tetrahydropyran-2-yl)oxy]bicyclo[3.1.0]hexane-6-carboxylate, on vapor phase chromatography on a 6-foot silicone rubber column at 200° C.; retention times 11 and 13 minutes.

A solution of 100 g. of the above oil is mixed with 21.4 g. of 25% methanolic sodium methoxide. The mixture is refluxed 4 hours, and then the methanol is evaporated. The residue is diluted with dichloromethane, and the resulting solution is washed with water, dried with anhydrous sodium sulfate, and evaporated under reduced pressure to give 80 g. of methyl 3-[(tetrahydropyran-2-yl)oxy]bicyclo[3.1.0]hexane-6-carboxylate.

Analysis: Calcd. for $C_{13}H_{20}O_4$: C, 64.98; H, 8.39. Found: C, 64.68; H, 8.42.

EXAMPLE 4

3-[(Tetrahydropyran-2-yl)oxy]bicyclo[3.1.0]hexane-6-carbinol (X, $R_4$=H, exo isomer)

A solution of methyl 3-[(tetrahydropyran-2-yl)oxy]-bicyclo[3.1.0]hexane-6-carboxylate (VIII, exo isomer, from Example 2) in diethyl ether is treated with excess lithium aluminum hydride in diethyl ether. Quantitative reduction results. Excess lithium aluminum hydride is decomposed by addition of water, and the diethyl ether solution is concentrated to give exo 3-[(tetrahydropyran-2-yl)oxy]bicyclo[3.1.0]hexane-6-carbinol as a viscous oil; b.p. 130°–135° C. at 0.05 mm.; γ 3400, 1140, and 1020 cm.$^{-1}$; δ 0.76 p.p.m. Thin layer chromatographic analysis (silica, developed with benzene-ether 5:1) shows two spots (syn and anti isomers).

EXAMPLE 5

3-[(Tetrahydropyran-2-yl)oxy]bicyclo[3.1.0]hexane-6-carbinol (X, $R_4$=H, exo isomer)

A solution of methyl 3-[(tetrahydropyran-2-yl)oxy]-bicyclo[3.1.0]hexane-6-carboxylate (VIII, exo isomer from Example 3) is added dropwise with stirring to a mixture of 8 g. of lithium aluminum hydride and 640 ml. of diethyl ether. The resulting mixture is stirred for 1 hour. Excess lithium aluminum hydride is then destroyed with water. The diethyl ether layer is separated, washed with water, and dried with anhydrous sodium sulfate. Evaporation of the diethyl ether under reduced pressure gives 32 g. of a colorless oil which is chromatographed on 3 kg. of silica gel. Elution with a mixture of isomeric hexanes and ethyl acetate (70:30) gives 15.5 g. of exo syn 3-[(tetrahydropyran-2-yl)oxy]-bicyclo[3.1.0]hexane-6-carbinol. Further elution with the same eluent gives 13.6 g. of exo anti 3-[(tetrahydropyran-2-yl)oxy]bicyclo[3.1.0]hexane-6-carbinol in the form of a colorless oil. These carbinols give retention times on vapor phase chromatography (6-foot 10% silicone rubber column at 160° C.) of 25 minutes for the syn isomer and 31 minutes for the anti isomer.

Analysis: Calcd. for $C_{12}H_{20}O_3$: C, 67.89; H, 9.50. Found for syn isomer: C, 68.21; H, 9.59. Found for anti isomer: C, 67.58; H, 9.61.

EXAMPLE 6

3-[(Tetrahydropyran-2-yl)oxy]bicyclo[3.1.0]hexane-6-carboxaldehyde (XI $R_4$=H, exo isomer)

A solution of 252 mg. of 3-[(tetrahydropyran-2-yl)oxy]bicyclo[3.1.0]hexane-6-carbinol (X, exo isomer from Example 4) in 10 ml. of acetone is cooled to −10° C., and 0.5 ml. of Jones reagent [Bowden et al., J. Chem. Soc. 39 (1946)], diluted with 0.5 ml. of acetone, is added dropwise with vigorous stirring over a period of 3 minutes. The mixture is stirred for another 5 minutes. Excess reagent is destroyed by addition of a few drops of isopropyl alcohol. The reaction mixture is then diluted with 50 ml. of water and extracted with diethyl ether. Evaporation of the diethyl ether extract gives 80% yield of exo 3-[(tetrahydropyran-2-yl)oxy]-bicyclo[3.1.0]hexane-6-carboxaldehyde in the form of an oil; $\gamma$ 3097, 3030, 2730, 1700, 1140, and 1020 $cm^{-1}$.; δ 9.2, 3.5, 4.15, 4.5 p.p.m.

The thus-obtained 3-[(tetrahydropyran-2-yl)oxy]-bicyclo-[3.1.0]hexane-6-carboxaldehyde is characterized as a dinitrophenylhydrazone, m.p. 202° C.

EXAMPLE 7

3-[(Tetrahydropyran-2-yl)oxy]bicyclo[3.1.0]hexane-6-carboxaldehyde (XI, $R_4$=H, exo syn isomer).

A solution of 12 g. of exo syn 3-[(tetrahydropyran-2-yl)-oxy]bicyclo[3.1.0]hexane-6-carbinol (from Example 5) in 400 ml. of acetone is cooled to −10° C. Jones reagent (24 ml. of a solution containing 10.3 g. $CrO_3$ and 8.7 ml. of concentrated sulfuric acid in 30 ml. of water) is added dropwise with stirring during 10 minutes. The reaction mixture is stirred an additional 15 minutes at −10° C., and then excess Jones reagent in the mixture is destroyed by addition of 14 ml. of isopropyl alcohol. The reaction mixture is then diluted with water and extracted four times with diethyl ether. The combined extracts are washed with aqueous sodium bicarbonate solution and then with water. After drying with anhydrous sodium sulfate, the diethyl ether is evaporated under reduced pressure to give 10 g. of exo syn 3-[(tetrahydropyran-2-yl)oxo]bicyclo[3.1.0]hexane-6-carboxaldehyde in the form of a colorless oil. The retention time on vapor phase chromatography (6-foot 10% silicone rubber column at 160° C.) is 23 minutes.

EXAMPLE 8

3-[(Tetrahydropyran-2-yl)oxy]bicyclo[3.1.0]hexane-6-carboxaldehyde (XI, $R_4$=H, exo anti isomer).

The procedure of Example 7 is followed, but the exo anti carbinol from Example 5 is used rather than the exo syn carbinol. The resulting exo anti carboxaldehyde gives a 29.5-minute retention on vapor phase chromatography.

EXAMPLE 9

3-[(Tetrahydropyran-2-yl)oxy]bicyclo[3.1.0]hexane-6-carboxylic acid (IX).

A mixture of 5 g. of methyl 3-[(tetrahydropran-2-yl)oxy]-bicyclo[3.1.0]hexane-6-carboxylate (VIII, syn and anti, from Example 3), ethanol (45 ml.), and sodium hydroxide (10 ml. of a 20% aqueous solution) is refluxed for 20 minutes. Cooling evaporation of the ethanol under reduced pressure, and addition of 100 ml. of water gives a solution which is acidified with dilute hydrochloric acid and extracted with diethyl ether. The diethyl ether extract is dried with anhydrous sodium sulfate and evaporated to give a mixture of exo syn and anti 3-[(tetrahydropyran-2-yl)oxy]bicyclo[3.1.0]hexane-6-carboxylic acid.

EXAMPLE 10

3-[(Tetrahydropyran-2-yl)oxy]-6-acetylbicyclo[3.1.0]hexane (XI $R_4$=$CH_3$).

A mixture of 4 g. of 3-[(tetrahydropyran-2-yl)oxy]-bicyclo[3.1.0]hexane-6-carboxylic acid (IX, from Example 9) and 25 ml. of thionyl chloride is refluxed for 15 minutes. The excess thionyl chloride is then removed under reduced pressure. The resulting acid chloride is dissolved in 50 ml. of benzene, and this solution is added to an equivalent amount of dimethylcadmium in benzene (J. Am. Chem. Soc. 71, 2136 (1949)). This mixture is refluxed 1 hour. Excess cold dilute hydrochloric acid is then added and the mixture is extracted with diethyl ether. The diethyl ether layer is separated, dried, and evaporated to give a mixture of exo syn and anti 3-[(tetrahydropyran-2-yl)oxy]-6-acetylbicylco[3.1.0]hexane.

Following the procedure of Example 10, the corresponding propionyl, butyryl, and isobutyryl compounds are obtained by using diethylcadmium, dipropylcadmium, and diisopropylcadmium respectively, in place of the dimethylcadmium.

EXAMPLE 11

3-[(Tetrahydropyran-2-yl)oxy]bicyclo[3.1.0]hexane-6-methylcarbinol (X, $R_4$=$CH_3$).

A solution of 0.55 mg. of sodium borohydride in 20 ml. of water is added to a solution of 5.0 g. of 3-[(tetrahydropyran-2-yl)oxy]-6-acetylbicyclo[3.1.0]hexane in 60 ml. of dimethylformamide at such a rate that the temperature does not rise above 20° C. The resulting mixture is stirred at 20° C. for 4 hours. The reaction mixture is then cooled, acidified with 10% aqueous acetic acid, and poured into 1500 ml. of water. The resulting aqueous mixture is extracted with diethyl ether. The diethyl ether extracts are dried over anhydrous sodium sulfate and then evaporated to give 3-[(tetrahydropyran-2-yl)oxy]bicyclo[3.1.0]hexane-6-methylcarbinol. This is a mixture of syn and anti isomers, and is used in the next step without purification.

Following the procedure of Example 11, the corresponding ethylcarbinol, propylcarbinol, and isopropylcarbinol are prepared by sodium borohydride reduction of the propionyl, and butyryl, and isobutyryl compounds, respectively.

EXAMPLE 12

6-(1-Heptenyl)-3-[(tetrahydropyran-2-yl)oxy]bicyclo[3.1.0]hexane (XII, $R_2$=pentyl, $R_3$ and $R_4$=H)

To 21.4 g. of hexyltriphenylphosphonium bromide [Cupas, Watts and Schleyer, Tetrahedron Letters, 2503 (1964)] in 300 ml. of dry diethyl ether at room temperature (about 25° C.) in a nitrogen atmosphere is added 19.5 ml. of a 22.22 wt. % solution of butyl lithium in hexane with stirring. After 10 minutes, 7 g. of exo 3-[(tetrahydropyran-2-yl)oxy]bicyclo[3.1.0]hexane-6-carboxaldehyde (from Example 6) in 20 ml. of dry diethyl ether is added, causing immediate precipitation. Most of the diethyl ether is evaporated, and 250 ml. of dry tetrahydrofuran is added. The reaction mixture is heated to 60–65° and stirred for 3 hours. Then, the solvent is evaporated and the residue is extracted several times with diethyl ether. The diethyl ether extracts are combined and washed twice with water, dried over magnesium sulfate, and evaporated to give a residue. This residue is chromatographed on aluminum oxide (activity II-III) and eluted with hexane-benzene 3:1 to give 9.5 g. of exo 6-(1-heptenyl)-3-[(tetrahydropyran-2-yl)oxy]bicyclo[3.1.0]hexane; $\gamma$3100, 3075, 3045, 1650, 1140, 1020, 850, and 735 cm$^{-1}$. Four isomers are present, cis-syn, cis-anti, trans-syn, and trans-anti, which are separated by chromatography on silica gel.

Following the procedure of Example 12 but using in place of the hexyltriphenylphosphonium bromide, 2-heptyltriphenylphosphonium bromide, pentyltriphenylphosphonium bromide, and propyltriphenylphosphonium bromide, there are obtained 6-(2-methyl-1-heptenyl)-3-[(tetrahydropyran-2-yl)oxy]bicyclo[3.1.0]hexane, 6-(1-hexenyl)-3-[tetrahydropyran-2-yl)oxy]bicyclo[3.1.0]hexane, and 6-(1-butenyl)-3-[(tetrahydropyran-2-yl)oxy]bicyclo[3.1.0]hexane, respectively. Also following the procedure of Example 12 but using in place of the carboxaldehyde from Example 6, 3-[(tetrahydropyran-2-yl)oxy]-6-acetylbicyclo[3.1.0]hexane (from Example 10) and the corresponding 6-propionyl, butyryl, and 6-isobutyryl compounds, there are obtained 6-(1-methyl-1-heptenyl)-3-[(tetrahydropyran-2-yl)oxy]bicyclo[3.1.0]hexane, and the corresponding 1-ethyl-1-heptenyl, 1-propyl-1-heptenyl, and 1-isopropyl-1-heptenyl compounds, respectively.

EXAMPLE 13

6-(1-Heptenyl)bicyclo[3.1.0]hexan-3-ol (XIII, $R_2$=pentyl, $R_3$ and $R_4$=H).

A solution of 8.5 g. of 6-(1-heptenyl)-3-[(tetrahydropyran-2-yl)oxy]bicyclo[3.1.0]hexane (from Example 12) and 700 mg. of oxalic acid in 350 ml. of methanol is stirred at room temperature (about 25° C.) for 7 days. The solution is then evaporated and the residue extracted with diethyl ether. Evaporation of the ether solution gives a quantitative yield of 6-(1-heptenyl)-bicyclo[3.1.0]hexan-3-ol; $\gamma$ 3375, 3050, 3025, 1625, 1070, 1020, 960, 850 and 725 cm$^{-1}$.; $\gamma$ max 197 mmu (heptane), $\delta$ 5.2, 4.8 p.p.m. Thin layer chromatographic analysis shows four spots (silica gel, developed with benzene-ether 5:1).

Following the procedure of Example 13, the other tetrahydropyran-2-yl compounds mentioned above after Example 12 are transformed to the corresponding hydroxy compounds.

EXAMPLE 14

6-(1-Heptenyl)bicyclo[3.1.0]hexan-3-ol (XIII, $R_2$=pentyl, $R_3$ and $R_4$=H).

A 15% solution of butyl lithium in hexane (45 ml.) is added under a nitrogen atmosphere to a stirred solution of 31 g. of hexyltriphenylphosphonium bromide in 400 ml. of benzene. The orange mixture is stirred for 15 minutes, after which 9.6 g. of exo syn 3-[(tetrahydropyran-2-yl)oxy]bicyclo[3.1.0]hexane-6-carboxaldehyde (from Example 7) dissolved in 70 ml. of benzene is added dropwise with stirring during 15 minutes. The resulting reaction mixture is heated and stirred for 3 hours at 60°–70° C. The mixture is then cooled and filtered, and the filtrate is washed with water, dried with anhydrous sodium sulfate, and evaporated to about a 100-ml. volume. This is diluted with an equal volume of an isomeric hexane mixture, and then filtered through silica gel. Evaporation gives 9.4 g. of an oily product which is refluxed one hour in 300 ml. of methanol containing 600 mg. of oxalic acid. The methanol is then removed under reduced pressure, and the residue is dissolved in diethyl ether. The diethyl ether solution is washed successively with aqueous sodium bicarbonate solution and water, and is dried with anhydrous sodium sulfate. Evaporation of the diethyl ether gives a residue which is chromatographed on silica gel. Elution with a mixture of isomeric hexanes and ethyl acetate (95:5) gives 3.3 g. of 6-exo(cis-1-heptenyl)-bicyclo[3.1.0]hexan-3-syn-ol. Further elution with the same eluent gives 0.7 g. of 6-exo-(trans-1-heptenyl)-bicyclo[3.1.0]-hexan-3-syn-ol. Vapor phase chromatography (6-foot 10% silicone rubber column at 170° C.) gives retention times of 9 minutes for the cis alcohol and 11 minutes for the trans alcohol.

Analysis: Calcd. for $C_{13}H_{22}O$ : C, 80.35; H, 11.41. Found for cis alcohol : C, 80.22; H, 11.26. Found for trans alcohol : C, 79.68; H, 11.44.

The procedure of Example 14 is also followed using exo anti 3-[(tetrahydropyran-2-yl)oxy]bicyclo[3.1.0-]hexane-3-carboxaldehyde (from Example 8). The resulting mixture of alcohols is chromatographed on a silica gel impregnated with 50% aqueous silver nitrate at 100° C. and dried at 110° C. Elution with a mixture of isomeric hexanes and ethyl acetate (85:15) gives 6-exo-(trans-1-heptenyl)bicyclo[3.1.0]hexane-3-antiol. Further elution with a mixture of isomeric hexanes and ethyl acetate (75:25) gives 6-exo-(cis-1-heptenyl)-bicyclo[3.1.0]hexane-3-antiol.

Analysis: Calcd. for $C_{13}H_{22}O$ : C, 80.35; H, 11.41. Found for cis alcohol : C, 80.11; H, 11.39. Found for trans alcohol : C, 80.70; H, 11.65.

EXAMPLE 15

6-(1-Heptenyl)-3-[(tetrahydropyran-2-yl)oxy]bicyclo[3.1.0]hexane (XII, $R_2$ = pentyl, $R_3$ and $R_4$ = H).

A solution of 1.43 g. of exo 3-[(tetrahydropyran-2-yl)oxy]bicyclo[3.1.0]hexane-6-carbinol (X, $R_4$ = H) and 5.56 g. triphenylphosphine hydrobromide in 50 ml. of dry tetrahydrofuran is stirred at room temperature (about 25° C.) for 46 hrs., during which time a precipitate forms. The precipitated phosphorane is separated by filtration, washed twice with cold tetrahydrofuran, and dried under reduced pressure over KOH pellets, giving a 30% yield of phosphorane melting at 149°–150° C., I.R. $\gamma$ = 1075, 1050, 1015, 1450, 1435, 1025, and 1040 cm.$^{-1}$.

90 mg. of sodium hydride (50% in oil) is washed with hexane, dried in a nitrogen stream, and added to 15 ml. of dimethylsulfoxide. The dispersion is kept under nitrogen at 70°–75° C. for 15 minutes (until evolution of hydrogen stops). Then 1 g. of the phosphorane obtained as above is added in one portion leaving a faint red solution. A solution of 200 mg. of hexanal in 5 ml. of dimethyl sulfoxide is added during 5 minutes and the mixture is stirred 5 hrs. at 70°–75° C. and 2 days at 50° C.; then ice and water is added. The mixture is extracted 3 times with diethyl ether, and the diethyl ether extracts are washed with water, dried over magnesium sulfate, and evaporated leaving a residue which is chromatographed over alumina (activity II–III) and eluted with benzene-hexane 1:3. Evaporation of the eluates gives the same exo 6-(1-heptenyl)-3-[(tetrahydropyran-2-yl)oxy]bicyclo[3.1.0]hexane described in Example 12.

Following the procedure of Example 15 but using in place of the 3-[(tetrahydropyran-2-yl)oxy]bicyclo[3.1.0]hexane-6-carbinol, the 3-[(tetrahydropyran-2-yl)oxy]bicyclo[3.1.0]hexane-6-methyl carbinol of Example 11, there is obtained the same 6-(1-methyl-1-heptenyl)-3-[(tetrahydropyran-2-yl)oxy]bicyclo[3.1.0]hexane mentioned after Example 12.

EXAMPLE 16

6-(1-Heptenyl)bicyclo[3.1.0]hexan-3-one (XIV, $R_2$ = pentyl, $R_3$ and $R_4$ = H).

Oxidation of 700 mg. of exo 6-(1-heptenyl)bicyclo[3.1.0]hexan-3-ol (Example 13) in acetone with excess Jones reagent, following the procedure of Example 6, gives an 85% yield of a residue which is chromatographed on aluminum oxide (activity II–III) and eluted with benzene-ether 5:1 to give a mixture of exo syn and anti isomers of 6-(1-heptenyl)bicyclo[3.1.0]hexan-3-one (XIV), $\lambda$ max 214 mmu, mass spectrum 192$^+$, 177$^+$, 174$^+$, 164$^+$, 163$^+$, 149$^+$, 150$^+$, 135$^+$, 122$^+$, 121$^+$, 109$^+$, 107$^+$, 136$^+$, 96$^+$, 93$^+$; $\delta$ 5.17, 5.32 (multiplets), 2.23 p.p.m.

Analysis:
Calcd. for $C_{13}H_{20}O$: C, 81.20; H, 10.48, mol. wt. 192.29. Found: C, 81.15; H, 10.40, mol. wt. 192 (mass spectrum).

Following the procedure of Example 16, each of the hydroxy compounds referred to following Example 13 is oxidized to the corresponding ketones.

EXAMPLE 17

6-Exo-(1-heptenyl)bicyclo[3.1.0]hexan-3-one (XIV, $R_2$ = pentyl, $R_3$ and $R_4$ = H)

A solution of Jones reagent (12 ml., see Example 7) is added dropwise under a nitrogen atmosphere during 10 minutes to a solution of 4.8 g. of 6-exo-(cis-1-heptenyl)bicyclo[3.1.0]hexan-3-syn-ol (Example 14) in 200 ml. of acetone. The resulting mixture is stirred 15 minutes at −10° C. Then, 15 ml. of isopropyl alcohol is added, and the mixture is diluted with water and extracted with dichloromethane. The extract is washed successively with aqueous sodium bicarbonate solution and water, dried, and evaporated under reduced pressure. The resulting oil is chromatographed on silica gel and eluted with a mixture of isomeric hexanes and dichloromethane (60:40) to give 3.5 g. of 6-exo-(cis-1-heptenyl)bicyclo[3.1.0]hexan-3-one.

Analysis: Calcd. for $C_{13}H_{20}O$: C, 81.20; H, 10.48. Found: C, 80.96, H, 10.43.

Following the procedure of Example 17, 6-exo-(cis-1-heptenyl)bicyclo[3.1.0]hexan-3-anti-ol (Example 14) is oxidized to the same 6-exo-(cis-1-heptenyl)bicyclo[3.1.0]hexan-3-one.

Also following the procedure of Example 17, 6-exo-(trans-1-heptenyl)bicyclo[3.1.0]hexan-3-syn-ol is oxidized to give 6-exo(trans-1-heptenyl)bicyclo[3.1.0]hexan-3-one.

Analysis: Calcd. for $C_{13}H_{20}O$: C, 81.20; H, 10.48. Found: C, 80.98; H, 10.57.

Following the above procedure, 6exo(trans-1-heptenyl)bicyclo[3.1.0]hexan-3-anti-ol is oxidized to the same 6-exo(trans-1-heptenyl)bicyclo[3.1.0]hexan-3-one.

EXAMPLE 18

6-Exo-(1-heptenyl)bicyclo[3.1.0]hexan-3-one (XIV, $R_2$ = pentyl, $R_3$ and $R_4$ = H)

Starting with 3-cyclopentenol and following the procedures of Examples 1, 3 (including isomerization), 5, 7, 14, and 17 but omitting all separations of stereoisomers, a mixture of cis and trans 6-exo(1-heptenyl)bicyclo[3.1.0]hexan-3-ones is obtained. This mixture is chromatographed on silica gel impregnated with 50% aqueous silver nitrate at 100° C. and dried at 110° C. Elution with a mixture of isomeric hexanes and ethyl acetate (94:6) gives 6-exo-(trans-1-heptenyl)bicyclo[3.1.0]hexan-3-one. Further elution with the same eluent but 92:8 gives 6-exo-(cis-1heptenyl)bicyclo[3.1.0]hexan-3-one. On thin layer chromatography (Adsorbosil-ADN-2/25% $AgNO_3$), the cis ketone has $R_f$ 0.51; the trans ketone has $R_f$ 0.66. Vapor pressure chromatography (6-foot 10% silicone rubber column, 170° C.) gives retention times 6 minutes for the cis ketone and 7 minutes for the trans ketone.

Following the chromatographic procedures set forth in Examples 17 and 18, each of the ketones referred to following Example 16 is separated into the individual exo-cis and exo-trans isomers.

EXAMPLE 19

Morpholino enamine of 6-exo-(1-heptenyl)bicyclo[3.1.0]hexan-3-one (XVI, $R_2$ = pentyl, $R_3$ and $R_4$ = H)

A mixture of 100 mg. of 6-exo-(1-heptenyl)bicyclo[3.1.0]hexan-3-one (from Example 16), 2 ml. of morpholine and a few crystals of p-toluenesulfonic acid in 0.5 ml. of benzene is refluxed under nitrogen for about 17 hrs., water being removed with a trap. After this period the mixture is cooled and washed with saturated aqueous sodium bicarbonate. The benzene layer is then separated, dried over sodium sulfate, and evaporated leaving a quantitative yield of the morpholino enamine of 6-(1-heptenyl)bicyclo[3.1.0]hexan-3-one; $\gamma$ 3100, 3075, 3050, 3025, 1625, 1120 and 732 cm$^{-1}$. This enamine is used without purification for the next step.

Following the procedure of Example 19 but using pyrrolidine, piperidine, and dibutyl amine separately in place of morpholine, there are obtained the corresponding pyrrolidino, piperidino, and dibutylamino enamines.

Also following the procedure of Example 19 but using separately in place of the 6-(1-heptenyl)bicyclo[3.1.0]hexan-3-one from Example 16, the corresponding 6-exo-(cis-1-heptenyl)bicyclo[3.1.0]hexane-3-one and 6-exo-(trans-1-heptenyl)bicyclo[3.1.0]hexane-3-one from Examples 17 or 18, there are obtained the corresponding morpholino enamines.

EXAMPLE 20

Ethyl 6-exo-(1-heptenyl)-3-oxobicyclo[3.1.0]hexane-2-heptanoate (XVa)

The enamine obtained by Example 19 is dissolved in 2 ml. of dry benzene, and 130 mg. of ethyl 7-iodoheptanoate in 10 ml. of benzene is added at 25° C. over a period of 30 minutes. The mixture is then heated under reflux for 40 hrs. under nitrogen, cooled, mixed with 40 ml. of water, and stirred for 2 hrs. The layers are separated and the water layer is extracted 3 times with benzene. The benzene extracts are combined and washed with ice cold 3% hydrochloric acid and then with water until neutral. The benzene solution is dried over magnesium sulfate and evaporated leaving 220 mg. of ethyl 6-exo-(1-heptenyl-3-oxobicyclo[3.1.0]hexane-2-heptanoate; $\gamma$ 3200, 3050, 3025, 1750, 1680, 1182 and 732 cm$^{-1}$. Thin layer chromatography shows a major spot of $R_f$ 0.62 (silica gel developed with chloroform) and a minor spot at $R_f$ 0.68.

EXAMPLE 21

Methyl 6-exo-(1-heptenyl)-3-oxobicyclo[3.1.0]hexane-2-heptanoate (XVa)

To a solution of 110 mg. of the enamine obtained according to Example 19 in 30 ml. of anhydrous dimethylsulfoxide is added all at once 500 mg. of methyl 7-iodoheptanoate. The mixture is stirred under nitrogen for 4 hours at 65°–75° C. After cooling, 30 ml. of water is added; and the mixture is stirred 4 hours at about 25° C. After further dilution with 300 ml. of water, the mixture is extracted with 4 portions of diethyl ether. The combined ether extracts are washed with water, dried, and evaporated under reduced pressure to give 338 mg. of a dark paste containing the desired methyl 6-exo-(1-heptenyl)-3-oxobicyclo[3.1.0]hexane-2-heptanoate plus some starting reactants. This paste is used without purification for subsequent reduction according to Example 27.

Following the procedure of Example 20, each of the other enamines mentioned after Example 19 is reacted separately with ethyl 7-iodoheptanoate to give the corresponding alkylated ketones XVa, i.e., $R_8$ is ethyl, $C_nH_{2n}$ is hexamethylene, and $-CR_4=CR_2R_3$ is cis-1-heptenyl, trans-1-heptenyl, 1-methyl-1-heptenyl, 1-ethyl-1-heptenyl, 1-propyl-1-heptenyl, 1-isopropyl-1-heptenyl, 2-methyl-1-heptenyl, 1-hexenyl, and 1-butenyl.

Also following the procedure of Example 20, but using separately in place of the ethyl 7-iodoheptanoate, ethyl 4-iodobutyrate, ethyl 5-iodopentanoate, ethyl 5-iodoheptanoate, ethyl 6-iodo-2,3-dimethylhexanoate, and ethyl 9-iodononanoate, there are obtained the corresponding alkylated ketones XVa, i.e., $R_8$ is ethyl, $-CR=CR_2R_3$ is 1-heptenyl, and $C_nH_{2n}$ is trimethylene, tetramethylene, 5-methylpentamethylene, 1,2-dimethylpentamethylene, and octamethylene.

EXAMPLE 22

Ethyl 6-exo-(1-heptenyl)-3-oxobicyclo[3.1.0]hexane-2-heptanoate (XVa) and 6-exo-(1-heptenyl)-3-oxobicyclo[3.1.0]hexane-2-heptanoic acid (XV, $R_1 = H$)

Potassium tert. butoxide is prepared by dissolving 21.72 mg. of potassium in 5 ml. of tert.-butanol and evaporating the solvent under nitrogen. The potassium tert.-butoxide residue is suspended in 10 ml. of benzene, and 100 mg. of 6-exo-(1-heptenyl)bicyclo[3.1.0]hexan-3-one (from Example 16) is added rapidly to the suspension while stirring. The mixture is heated under reflux for 30 min.; then 134 mg. of ethyl 7-bromoheptanoate is added dropwise (through a syringe) during a 30-minute period. Heating is continued for 6.5 hrs. Then the mixture is cooled, and ice water is added, followed by one drop of concentrated hydrochloric acid. The aqueous and organic layers are separated, and the aqueous layer is extracted first with diethyl ether and then with ethyl acetate. The organic extracts are combined, dried with anhydrous sodium sulfate, and evaporated to give 190 mg. of ethyl 6-exo-(1-heptenyl)-3-oxobicyclo[3.1.0]hexane-2-heptanoate.

The thus obtained heptanoate is suspended in 7 ml. of 2.5% aqueous sodium carbonate solution, and stirred at 120° C. bath temperature for 3.5 hrs. Then the mixture is cooled, diluted with 10 ml. of water, and extracted 3 times with diethyl ether. The aqueous layer is cooled, and made acid, and then extracted successively with chloroform and ethyl acetate. The combined organic extracts are dried over anhydrous sodium sulfate and evaporated to give a residue which is chromatographed on 5 g. of silica gel and eluted with benzene. Evaporation of the eluates gives 6-exo-(1-heptenyl)-3-oxobicyclo[3.1.0]hexane-2-heptanoic acid; $\gamma$ 3050, 3025, 1750, 1715, 1625, 1170, and 735 cm$^{-1}$., $\lambda$ max 213 mmu (ethanol).

EXAMPLE 23

Methyl 6-exo-(1-heptenyl)-3-oxobicyclo[3.1.0]hexane-2-heptanoate (XVa)

To a solution of 4 equivalents of potassium tert-butoxide in 15 ml. of 1,2-dimethoxyethane is added 100 mg. of 6-exo-(1-heptenyl)bicyclo[3.1.0]hexan-3-one (from Example 16). A solution of 6 equivalents of methyl 7-iodoheptanoate in 2 ml. of dry 1,2-dimethoxyethane is injected with a syringe (nitrogen atmosphere). The mixture is refluxed and stirred, following the progress of the reaction by subjecting samples of the reaction mixture to thin layer chromatograhy. The desired compound XVa starts to form after 6 hours and reaches a maximum at about 25 hours at which time the reaction mixture is cooled, diluted with ice water, acidified with dilute hydrochloric acid, and extracted with diethyl ether. The diethyl ether extract is dried and evaporated to give an oil. The oil is chromatographed on 3.5 g. of aluminum oxide (activity II-III). The starting iodo ester is eluted with hexane-benzene (3:1). Further elution with benzene gives the desired methyl 6-exo-(1-heptenyl)-3-oxobicyclo[3.1.0]hexane-2-heptanoate plus some of the reactant ketone. This mixture is used without further separation for subsequent reduction according to Example 27.

EXAMPLE 24

Methyl 6-exo-(trans-1-heptenyl)-3-oxobicyclo[3.1.0]hexane-2-heptanoate (XVa)

A mixture of 5.00 g. of 6-exo-(trans-1-heptenyl)bicyclo[3.1.0]hexan-3-one (from Example 17), 21.0 g. of methyl iodoheptanoate, and 500 ml. of tetrahydrofuran is stirred and cooled at +5° C. under an atmosphere of nitrogen. A solution of 3.80 g. of potassium tert-butoxide in 1 l. of tetrahydrofuran is added with stirring at +5° C. during 60 minutes. After the addition is complete, and the reaction mixture starts to turn brown and deposit a white precipitate of potassium iodide, 50 ml. of 5% hydrochloric acid is added. The mixture is then concentrated at reduced pressure (40° C. bath) to 350 ml., diluted with 200 ml. of water, and extracted with 3 successive 200-ml. portions of ethyl acetate. The combined extracts are washed first with 150 ml. of 5% aqueous sodium thiosulfate and then with aqueous sodium chloride solution, and are then dried with anhydrous magnesium sulfate. Evaporation at reduced pressure gives an oil which is stripped of unreacted iodo ester and unreacted ketone at 40–70 microns pressure. The residual oil is chromatographed on 1 kg. of silica gel. After elution with 5 l. of isomeric hexanes, 5 l. of a mixture of isomeric hexanes and ethyl acetate (97.5;2.5), and 5 l. of a mixture of isomeric hexanes and ethyl acetate (95:5), further elution with 3 l. of the 3rd eluent gives on evaporation 1.23 g. of the alpha isomer of methyl 6-exo-(trans-1-heptenyl)-3-oxobicyclo[3.1.0]hexane-2-heptanoate. After elution with another l. of the 3rd. eluent, further elution with 5 l. of the same eluent gives on evaporation 0.813 g. of the beta isomer of methyl 6-exo-(trans-1-heptenyl)-3-oxobicylco[3.1.0]hexane-2-heptanoate.

Following the procedure of Example 24 but using 8.00 g. of 6-exo-(cis-1-heptenyl)bicyclo[3.1.0]hexan-3-one (from Example 17) in place of the trans ketone, and corresponding larger amounts of diluents and other reactants, there are obtained 15.1% yield of the alpha isomer of methyl 6-exo-(cis-1-heptenyl)-3-oxobicyclo[3.1.0]hexane-2-heptanoate and 17.7% yield of the beta isomer of methyl 6-exo-(cis-1-heptenyl)-3-oxobicyclo[3.1.0]hexane-2-heptanoate.

EXAMPLE 25

Methyl 6-exo-(1-heptenyl)-3-hydroxybicyclo[3.1.0]hexane-2-heptanoate. (XVII)

A solution of methyl 6-(1-heptenyl)-3-oxobicyclo[3.1.0]hexane-2-heptanoate (500 mg., prepared according to Example 20) in 26 ml. of dimethylformamide is mixed slowly with sodium borohydride (110 mg.) in 6.5 ml. of water in the range 20° to 22° C. The resulting mixture is stirred at 20° C. for 4 hours, and is then cooled and mixed with an equal volume of 10% aqueous acetic acid. That mixture is poured into 500 ml. of water, and the resulting suspension is extracted 4 times with diethyl ether. The combined extracts are dried with anhydrous sodium sulfate and evaporated. The residue is subjected to preparative thin layer chromatography on silica gel with hexane-acetone (4:3). The material with $R_f$ 0.33 is eluted to give methyl 6-exo-(1-heptenyl-3-hydroxybicyclo[3.1.0]hexane-2-heptanoate. I. R. 3400, 3100, 3075, 3030, 1020, 1745, and 1180 cm$^{-1}$. This exo product is a mixture of alpha- and beta-isomers which is separated by further thin layer chromatrography on silica gel.

EXAMPLE 26

6-Exo-(1-heptenyl)-3-hydroxybicyclo[3.1.0]hexane-2-heptanoic acid (XVII)

A solution of methyl 6-(1-heptenyl)-3-hydroxybicyclo[3.1.0]hexane-2-heptanoate (17 mg.) from Example 25 in 5 ml. of methanol containing 0.5 ml. of 10% aqueous sodium carbonate solution is heated at 55° C. for 2 hours. The resulting mixture is then cooled to 0° C., acidified with hydrochloric acid to pH 2, and extracted wtih diethyl ether. The diethyl ether solution is washed, dried with anhydrous sodium sulfate, and evaporated to give 6-(1-heptenyl)-3-hydroxybicyclo[3.1.0]hexane-2-heptanoic acid. I. R. 1745 and 1700 cm$^{-1}$.

EXAMPLE 27

Methyl 6-exo-(1-heptenyl)-3-hydroxybicyclo[3.1.0]hexane-2-heptanoate (XVII)

The dark paste from Example 21 is dissolved in 4 ml. of dimethylformamide and cooled to 20° C. A solution of 2 equivalents of sodium borohydride in 1 ml. of water is added dropwise below 20° C. The resulting mixture is stirred 4 hours. Excess borohydride is then destroyed with 10% aqueous acetic acid. Diethyl ether extraction followed by evaporation gives 300 mg. of a colorless oil which is chromatographed on 7 g. of aluminum oxide (activity II-III). After elution with hexane, further elution with benzene-diethyl ether (1:1) gives methyl 6-exo-(1-heptenyl)-3-hydroxybicyclo[3.1.0]hexane-2-heptanoate. Thin layer chromatography on silica gel impregnated with 3% silver nitrate and diethyl ether-benzene (6:4) gives $R_f$ 0.33 I. R. 3400, 3095, 3085, 3075, 3045, 1745, 1615, 1242 cm$^{-1}$.

EXAMPLE 28

6-Exo-(1-heptenyl)-3-hydroxybicyclo[3.1.0]hexane-2-heptanoic acid (XVII)

The methyl ester (20 mg.) from Example 27 is dissolved in 5 ml. of methanol and stirred 4 hours with 15 mg. of sodium hydroxide at 25° C. The mixture is then diluted with ice water and extracted with diethyl ether. The aqueous alkaline layer is then acidified with dilute hydrochloric acid and extracted with diethyl ether. The extract is dried and evaporated to give 6-exo-(1-heptenyl)-3-hydroxybicyclo[3.1.0]hexane-2-heptanoic acid.

EXAMPLE 29

Methyl 6-exo-(cis-1-heptenyl)-3-hydroxybicyclo[3.1.0]hexane-2α-heptanoate (XVII)

A solution of 175 mg. of methyl 6-exo-(cis-1-heptenyl)-3-oxobicyclo[3.1.0]hexane-2α-heptanoate (from Example 24) in 8 ml. of isopropyl alcohol is cooled with an ice bath. A solution of 100 mg. of sodium borohydride in 1.5 ml. of water is added rapidly with stirring. The mixture is stirred for 2.25 hours with cooling. Acetone (2 ml.) is then added and, after a few minutes, a solution of 0.5 ml. of acetic acid in 10 ml. of water is added. The mixture is concentrated and extracted with ethyl acetate. The extract is washed with aqueous sodium chloride solution, and is then dried and evaporated to give an oil which is chromatographed on 17 g. of Florisil (magnesium silicate). Elution with a mixture of isomeric hexanes and acetone (97:3) gives 60 mg. of the beta alcohol and 27 mg. of the alpha alcohol. Thin layer chromatography on silica gel with cyclohexane-ethyl acetate (75:25) gives $R_f$ 0.49 for the beta alcohol and $R_f$ 0.40 for the alpha alcohol.

EXAMPLE 30

Methyl 6-exo-(cis-1-heptenyl)-3-hydroxybicyclo[3.1.0]hexane-2β-heptanoate (XVII)

A solution of 600 mg. of methyl 6-exo-(cis-1-heptenyl)-3-oxobicyclo[3.1.0]hexane-2β-heptanoate (from Example 24) in 25 ml. of isopropyl alcohol is cooled with an ice bath. A solution of 500 mg. of sodium borohydride in 3 ml. of water is added rapidly with stirring. The ice bath is removed, and the mixture stirred for 3.5 hours. A solution of 1 ml. of acetic acid in 25 ml. of water is then added in small portions, after which the mixture is concentrated at reduced pressure to ½ volume and extracted with ethyl acetate. The extract is washed with aqueous sodium chloride solution, dried, and evaporated to give an oil which is chromatographed on 50 g. of Florisil. Elution with a mixture of isomeric hexanes and acetone (97.5:2.5) gives 58 mg. of the beta alcohol. Further elution with the same solvent system but 95:5 gives 78 mg. of the alpha alcohol. Thin layer chromatography on silica gel with cyclohexane-ethyl acetate (75:25) gives $R_f$ 0.58 for the beta alcohol and $R_f$ 0.38 for the alpha alcohol.

EXAMPLE 31

Methyl 6-exo-(cis-1-heptenyl)-3-hydroxybicyclo[3.1.0]hexane-2α-heptanoate

A solution of sodium borohydride (100 mg.) in 1.5 ml. of water is added to a solution of methyl 6-exo-(cis-1-heptenyl)-3-oxobicyclo[3.1.0]hexane-2α-heptanoate (175 mg., from Example 24) in 8 ml. of isopropyl alcohol with stirring at 0° C. The mixture is stirred 2.25 hours at 0° C. Acetone (2 ml.) is added and, after a few minutes, a solution of acetic acid (0.5 ml.) in 10 ml. of water is added. The resulting mixture is concentrated under reduced pressure and then extracted with ethyl acetate. The extract is washed, dried, and evaporated. The residue is chromatographed on 25 g. of silica gel, eluting with increasing concentrations of ethyl acetate in Skellysolve B (a mixture of isomeric hexanes) to give first the 3β-hydroxy product (125 mg.; $R_f$ 0.18 on silica gel thin layer plates developed twice with 25% ethyl acetate-cyclohexane), and then the 3α-hydroxy product (15 mg., $R_f$ 0.16 on the same tlc system).

EXAMPLE 32

Methyl 6-exo-(cis-1-heptenyl)-3-hydroxybicyclo[3.1.0]hexane-2β-heptanoate

A solution of sodium borohydride (225 mg.) in 2 ml. of water is added to a solution of methyl 6-exo-(cis-1-heptenyl)-3-oxobicyclo[3.1.0]hexane-2β-heptanoate (225 mg., from Example 24) in 25 ml. of isopropyl alcohol with stirring at 0° C. The mixture is stirred 2 hours at 0° C. Acetic acid (1 ml.) in 10 ml. of water is then added, and the mixture is concentrated under reduced pressure and extracted with ethyl acetate. The extract is washed, dried, and evaporated. The residue is chromatographed on 125 g. of Florisil, eluting with increasing concentrations of acetone in Skellysolve B to give first the 3β-hydroxy product (177 mg.; $R_f$ 0.21 on silica gel thin layer plates developed twice with 25% ethyl acetate-cyclohexane; infrared absorption at 3450, 2990, 1745, 1650, 1190, 1050, 840, and 720 cm$^{-1}$; nmr peaks at 5.26, 4.80, 4.18, and 3.68 δ), and then the 3α-hydroxy product (243 mg.; $R_f$ 0.14 on the same tlc system; similar infrared absorption and nmr except nmr has peak at 3.45 instead of 4.18).

EXAMPLE 33

Methyl 6-exo-(trans-1-heptenyl)-3-hydroxybicyclo[3.1.0]hexane-2α-heptanoate

Following the procedure of Examples 31 and 32, methyl 6-exo-(trans-1-heptenyl)-3-oxobicyclo[3.1.0]hexane-2α-heptanoate (Example 24) is reduced to a 1:9 ratio of the 3α- and 3β-hydroxy products. This mixture is separated as described in Example 31. Infrared absorption for both products at 3325, 1740, 1190, 1160, 1060, and 960 cm$^{-1}$.

EXAMPLE 34

Methyl 6-exo-(trans-1-heptenyl)-3-hydroxybicyclo[3.1.0]hexane-2β-heptanoate

Following the procedure of Examples 31 and 32, methyl 6-exo-(trans-1-heptenyl)-3-oxobicyclo[3.1.0]hexane-2β-heptanoate (Example 24) is reduced to a 45:55 ratio of the 3α- and 3β-hydroxy products. This mixture is separated as described in Example 32. Infrared absorption same as for the products of Example 33.

EXAMPLE 35

Methyl 6-exo(1,2-epoxyheptyl)-3α-hydroxybicyclo[3.1.0]hexane-2α-heptanoate

A solution of mixed cis and trans isomers of methyl 6-exo(1-heptenyl)-3α-hydroxybicyclo[3.1.0]hexane-2α-heptanoate (0.71 g., 80% cis) in dichloromethane (50 ml.) is mixed with 0.52 g. of m-chloroperbenzoic acid in one portion at 0°C. After stirring 30 minutes, an additional 50 mg. of m-chloroperbenzoic acid is added, and the mixture is stirred an additional 15 minutes. The mixture is then washed successively with ice-cold aqueous solutions of sodium bicarbonate, sodium iodide, and sodium thiosulfate, dried, and evaporated to give 0.77 g. of an amber oil. A portion (150 mg.) of this oil is chromatographed on 10 g. of silica gel, eluting with 30% ethyl acetate in cyclohexane to give 122 mg. of the desired epoxide; nmr peaks at 3.9, 3.58, and 0.58 δ.

EXAMPLE 36

Methyl 6-exo-(1,2-epoxyheptyl)-3β-hydroxybicyclo[3.1.0]hexane-2α-heptanoate

Following the procedure of Example 35, a mixture of the cis and trans isomers of methyl 6-exo-(1-heptenyl)-3β-hydroxybicyclo[3.1.0]hexane-2α-heptanoate is epoxidized to the corresponding 1,2-epoxyheptyl product.

EXAMPLE 37

Methyl 6-exo-(1,2-epoxyheptyl)-3α-hydroxybicyclo[3.1.0]hexane-2β-heptanoate.

Following the procedure of Example 35, a mixture of the cis and trans isomers of methyl 6-exo-(1-heptenyl)-3α-hydroxybicyclo[3.1.0]hexane-2β-heptanoate is epoxidized to the corresponding 1,2-epoxyheptyl product; nmr peaks at 3.62, 3.18, and 0.50 δ.

EXAMPLE 38

Methyl 6-exo-(1,2-epoxyheptyl)-3β-hydroxybicyclo[3.1.0]hexane-2β-heptanoate.

Following the procedure of Example 35, a mixture of the cis and trans isomers of methyl 6-exo-(1-heptenyl)-3β-hydroxybicyclo[3.1.0]hexane-2β-heptanoate is epoxidized to the corresponding 1,2-epoxyheptyl product; nmr peaks at 4.08, and 3.62 δ.

Also following the procedure of Example 35, each of the individual cis and trans isomers of the various 1-heptenyl reactants mentioned in Examples 35, 36, 37, and 38 is epoxidized to the corresponding 1,2-epoxyheptyl product.

EXAMPLE 39 dl-Prostaglandin $F_{1\alpha}$ Methyl Ester

A solution of the epoxide of Example 35 (400 mg.) in 15 ml. of recrystallized formic acid is maintained 16 hours at 25° C. Formic acid is removed from the deep purple solution under reduced pressure. The residue is dissolved in a mixture of 30 ml. of methanol and 10 ml. of water. Oxygen is purged from this solution by bubbling nitrogen through the solution for 3 minutes. Then, sodium carbonate (3 g.) is added, and the mixture is stirred at 25° C, for 1.5 hours. The mixture is acidified with dilute hydrochloric acid and evaporated under reduced pressure. The residue is extracted with dichloromethane, and the extract is washed, dried, and evaporated. The residue is combined with 60 mg. of residue obtained in the same manner, and the combined residues are chromatographed on 40 g. of silica gel, eluting with 200 ml. of 20% ethyl acetate in cyclohexane, 200 ml. of 40% ethyl acetate in cyclohexane, 200 ml. of 60% ethyl acetate in cyclohexane, 200 ml. of 80% ethyl acetate in cyclohexane, 400 ml. of ethyl acetate, and 400 ml. of ethyl acetate containing 5% methanol, collecting 40-ml. fractions. Fractions 23–27 are combined and evaporated to give 85 mg. of a mixture of dl-15-epi-PGF$_{1\alpha}$ methyl ester and a glycol. Fractions 31-40 are combined and evapoated to give 74 mg. of a mixture of dl-PGF$_{1\alpha}$ methyl ester and a glycol.

The residue from fractions 23–27 is mixed with excess sodium periodate in aqueous methanol at 25° C., and the resulting mixture is evaporated under reduced pressure. The residue is extracted with ethyl acetate. The extract is washed, dried, and evaporated. The residue is chromatographed on silica gel as above to give 15 mg. of dl-15-epi-PGF$_{1\alpha}$ methyl ester.

The residue from fractions 31–40 is chromatographed on 15 g. of acid-washed silica gel, eluting with 60 ml. of 33% ethyl acetate in cyclohexane, 60 ml. of 50% ethyl acetate in cyclohexane, 120 ml. of 66% ethyl acetate in cyclohexane, 75 ml. of ethyl acetate, 60 ml. of ethyl acetate containing one % methanol, 60 ml. of ethyl acetate containing 2% methanol, 60 ml. of ethyl acetate containing 3% methanol, and 60 ml. of ethyl acetate containing 5% methanol, collecting 15-ml. fractions. Fractions 23, 24, and 25 are combined and evaporated, and the residue is chromatographed as above to give 17 mg. of residue. That residue is combined with the residue resulting from the evaporation of combined fractions 26–31. The combined residues are applied equally to four 8 × 8 inch tlc plates (Brinkman, thin-coated abrasive resistant coated with silica gel F) which have been sprayed with 10% boric acid in methanol and then dried 1 hour at 100° C. The plates are developed twice with ethyl acetate. The separated bands are visualized by brief exposure to iodine vapor, and then scraped off, extracted with a methanol-ethyl acetate (1:1) mixture, and filtered. The filtrate is evaporated, extracted with diethyl ether, and filtered. The filtrate is evaporated. The resulting residue from the less polar band is dl-PGF$_{1\alpha}$ methyl ester (12 mg.); m.p. 70°–73° C. after recrystallization from a mixture of diethyl ether and Skellysolve B; infrared absorption at 3400, 1745, 1200, 1175, 1070, and 975 cm$^{-1}$; nmr peaks at 5.5, 4.1, 3.67, and 0.87 δ.

EXAMPLE 40 dl-Prostaglandin $F_{1\beta}$ Methyl Ester

A solution of the epoxide of Example 36 (100 mg.) in 2 ml. of trifluoroacetic acid is warmed at 40° C. for 10 minutes. The dark solution is evaporated under reduced pressure to a dark oil which is hydrolyzed with sodium carbonate in methanol as described in Example 39. The resulting residue is chromatographed on 10 g. of silica gel, eluting successively with 20, 40, 60, and 80% ethyl acetate in cyclohexane, and then with 100% ethyl acetate and ethyl acetate containing 5 and 10% methanol. The second and third products to be eluted from the column (100% ethyl acetate and thereafter) are dl-15-epi-PGF$_{1\beta}$ methyl ester (13 mg.) and dl-PGF$_{1\beta}$ methyl ester (17 mg.). The latter is rechromatographed to give dl-PGF$_{1\beta}$ methyl ester; m.p. 101°-102° C. after recrystallization from a mixture of acetone and Skellysolve. B; infrared absorption at 3350, 1745, 1240, 1200, 1170, 1080, 1030, and 970 cm$^{-1}$; nmr peaks at 5.55, 4.0, 3.68, 3.3, and 0.9 δ.

EXAMPLE 41 dl-8-Isoprostaglandin $F_{1\alpha}$ Methyl Ester

A solution of the epoxide of Example 37 (1.75 g.) is treated with formic acid (20 ml.) and the product is hydrolyzed with sodium carbonate as described in Example 39. Chromatography of the product on 100 g. of silica gel, eluting with increasing concentrations of ethyl acetate in cyclohexane, followed by elution with ethyl acetate and then ethyl acetate containing 5% methanol gives with the last eluates dl-8-iso-PGF$_{1\alpha}$ (177 mg.); m.p. 83°–84° C. after recrystallization first from a mixture of acetone and Skellysolve B and then from diethyl ether; infrared absorption at 3225, 1745, 1200, 1175, 1095, 1070, 970, and 730 cm$^{-1}$ ; nmr peaks at 5.5, 4.0, 3.65, 3.1, 2.3, and 0.9 δ. dl-8-iso-15-epi-PGF$_{1\alpha}$ is also isolated from earlier (less polar) eluates.

EXAMPLE 42 dl-8-Isoprostaglandin $F_{1\beta}$ Methyl Ester

A solution of the epoxide of Example 38 (1.53 g.) is treated with formic acid and the product is hydrolyzed and chromatographed as described in Example 41 to give dl-8-iso-$PGF_{1\beta}$ (145 mg.); m.p. 93°–94° C. after recrystallization first from a mixture of acetone and Skellysolve B and then from diethyl ether; infrared absorption at 3225, 1745, 1320, 1210, 1170, 1040, 1020, 970, and 865 cm$^{-1}$; nmr peaks at 5.55, 4.2, 3.6, 2.85, and 0.9. dl-8-iso-15-epi-$PGF_{1\beta}$ is also isolated from earlier (less polar) eluates.

EXAMPLE 43 dl-8-Isoprostaglandin $F_{1\alpha}$ dl-8-Isoprostaglandin $PGF_{1\alpha}$ methyl ester (15 mg., Example 41) is hydrolyzed with aqueous methanolic solium hydroxide (0.2N) at 50° C. to give, after acidification and isolation, dl-8-iso-$PGF_{1\alpha}$.

EXAMPLE 44 dl-8-isoprostaglandin $F_{1\beta}$

Following the procedure of Example 43, dl-8-iso-$PGF_{1\beta}$ methyl ester is saponified to dl-8-iso-$PGF_{1\beta}$.

EXAMPLE 45 dl-$PGF_{1\alpha}$ and dl-$PGF_{1\beta}$ Methyl Esters

A solution of methyl 6-exo-(1-heptenyl)-3-hydroxybicyclo[3.1.0]hexane-2-heptanoate (25 mg., from Example 27) in 3 ml. of ice-cold formic acid is mixed with 1.1 equivalents of 30% aqueous hydrogen peroxide in an atmosphere of nitrogen. The resulting mixture is allowed to warm slowly to about 25° C. during 2.5 hours, and is then stirred at about 40° C. for 1.5 hours. The resulting mixture is evaporated under reduced pressure, and the residue is mixed with 3 ml. of 3% aqueous sodium bicarbonate solution. That mixture is shaken for 1.5 hours at about 25° C., acidified to pH 2, and extracted with diethyl ether. The diethyl ether extract is washed with successive portions of water until a fresh washing is neutral, and is then dried with anhydrous sodium sulfate and evaporated to dryness. The oily residue is subjected to preparative thin layer chromatography on silica gel impregnated with 3% aqueous silver nitrate solution, using as solvent system ethyl acetate-methanol-water (160:25:100). Two compound zones are obtained which are separately eluted and isolated in the usual manner. The faster moving zone, $R_f$ 0.62, contains racemic methyl 7-[3α,5α-dihydroxy-2-(3-hydroxy-1-octen)-cyclopent-1α-yl]heptanoate ($PGF_{1\alpha}$). The slower moving zone contains the corresponding β-isomer ($PGF_{1\beta}$).

EXAMPLE 46 dl-$PGF_{1\alpha}$ and dl-$PGF_{1\beta}$

A solution of 6-exo-(1-heptenyl)-3-hydroxybicyclo[3.1.0]-hexane-2-heptanoic acid (27 mg., from Example 26) in 3 ml. of ice-cold formic acid containing 6 equivalents of sodium formate is mixed with 1.1 equivalents of 30% aqueous hydrogen peroxide in an atmosphere of nitrogen. The resulting mixture is allowed to warm slowly to about 25° C. during 2.5 hours, and is then stirred at about 40° C. for 1.5 hours. The resulting mixture is evaporated under reduced pressure to give a powdery residue which is shaken with 3 ml. of saturated aqueous sodium bicarbonate solution for 2.5 hours. The resulting solution is acidified with dilute hydrochloric acid to pH 2. Diethyl ether extraction and evaporation of the extract gives a residue which is subjected to preparative thin layer chromatography on silica gel impregnated with 3% aqueous silver nitrate solution, using as solvent system ethyl acetate-methanol-acetic acid-isooctanewater (110:30:35:10:100). Two compound zones are obtained which are separately eluted and isolated in the usual manner. The faster moving zone contains racemic 7-[3α,5α-dihydroxy-2-(3-hydroxy-1-octen)cyclopent-1α-yl]heptanoic acid ($PGF_{1\alpha}$), and has the same $R_f$ as authentic natural $PGF_{1\alpha}$. The mass spectrum and infrared spectrum of the material in the faster moving zone are the same as for authentic natural $PGF_{1\alpha}$. This racemic $PGF_{1\alpha}$ shows 40% of the activity of authentic natural $PGF_{1\alpha}$ when tested for smooth muscle stimulating activity on the rat stomach fundus preparation.

The slower moving zone contains racemic 7-[3α,5β-dihydroxy-2-(3-hydroxy-1-octen)-cyclopent-1α-yl]heptanoic acid ($PGF_{1\beta}$).

EXAMPLE 47 dl-$PGF_{1\alpha}$

A solution containing 20 mg. of 6-exo-(1-heptenyl)-3-hydroxybicyclo[3.1.0]hexane-2-heptanoic acid (from Example 28) in 2 ml. of formic acid containing 5 equivalents of sodium bicarbonate (based on the heptanoic acid) is cooled to 0° C. An equivalent amount of hydrogen peroxide is added, and the solution is stirred for 1 hour while warming to 25° C. The mixture is again cooled and then evaporated. Saturated aqueous sodium bicarbonate (3 ml.) is added to the residue, and the suspension is shaken 45 minuted. After extraction with diethyl ether, the solution is cooled to 5° C., acidified to pH 3 with 1 N hydrochloric acid, and at once extracted with several portions of diethyl ether. The combined exracts are washed with small amounts of water and are then dried and evaporated to give 17 mg. of an oil. Thin layer chromatography of this oil on silica gel containing 3% silver nitrate with ethyl acetateacetic acid-methanol-trimethylpentane-water (110:30:35:10:100) gives racemic $PGF_{1\alpha}$, $R_f$ 0.65. This product shows 40% of the activity of natural optically active $PGF_{1\alpha}$ on bioassay when tested for smooth muscle stimulating activity on the rat stomach fundus preparation.

Following the procedures of Examples 35 to 47, each of the other formula XVII reactants described above in and after the various preceeding Examples, including the individual racemic and optically active stereoisomers, is transformed to the corresponding formula V $PGF_1$-type product.

Also following the procedures of Examples 35 to 47, the 1-methyl-1-heptenyl, 1-ethyl-1-heptenyl, 1-propyl-1-heptenyl, 1-isopropyl-1-heptenyl, 2-methyl-1-heptenyl, 1-hexenyl, 1-butenyl, trimethylene, tetramethylene, 5-methyltetramethylene, 5-methylpentamethylene, 1,2-dimethylpentamethylene, and octamethylene analogs described after Example 21 are each transformed after borohydride reduction, to formula V $PGF_1$-type products.

We claim:

1. A compound of the formula

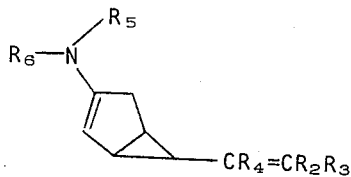

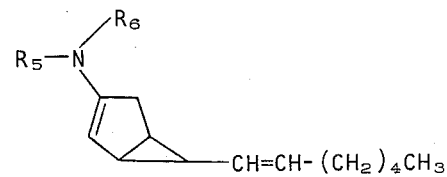

wherein $R_2$ is alkyl of 4 to 8 carbon atoms, inclusive, wherein $R_3$ and $R_4$ are hydrogen or methyl, and wherein $R_5$ and $R_6$ are alkyl of one to 8 carbon atoms, inclusive.

2. A compound according to claim 1 wherein $R_5$ and $R_6$ are both butyl.

3. A compound of the formula wherein $R_5$ and $R_6$ are alkyl of one to 8 carbon atoms, inclusive.

4. A compound according to claim 3 wherein $R_5$ and $R_6$ are both butyl.

* * * * *